United States Patent
Kim et al.

(10) Patent No.: US 10,117,903 B1
(45) Date of Patent: Nov. 6, 2018

(54) METHOD FOR REGULATING CANCER STEM CELL GROWTH BY INHIBITING PHOSPHORYLATION OF 120TH THREONINE RESIDUE OF TSPYL5 PROTEIN, A COMPOSITION CONTAINING THE PEPTIDE SEQUENCE FUNCTIONING TO INHIBIT THE PHOSPHORYLATION AND A USE THEREOF

(71) Applicant: Korea Atomic Energy Research Institute, Daejeon (KR)

(72) Inventors: In Gyu Kim, Daejeon (KR); Seo Yeon Kim, Daejeon (KR); Jei Ha Lee, Daejeon (KR); Soo Im Choi, Daejeon (KR); Min Sik Kim, Sejong (KR); Jung Yul Kim, Daejeon (KR); Byungchul Shin, Seoul (KR); Uhee Jung, Gyeonggi-do (KR)

(73) Assignee: Korea Atomic Energy Research Institute, Daejeon (KR)

( * ) Notice: Subject to any disclaimer, the term of this patent is extended or adjusted under 35 U.S.C. 154(b) by 0 days.

(21) Appl. No.: 15/774,208

(22) PCT Filed: Jun. 15, 2017

(86) PCT No.: PCT/KR2017/006240
§ 371 (c)(1),
(2) Date: May 7, 2018

(87) PCT Pub. No.: WO2017/217782
PCT Pub. Date: Dec. 21, 2017

(30) Foreign Application Priority Data

Jun. 15, 2016 (KR) .......................... 10-2016-0074655

(51) Int. Cl.
| | | |
|---|---|---|
| A61K 38/00 | (2006.01) | |
| A61K 38/02 | (2006.01) | |
| A61P 35/04 | (2006.01) | |
| C07K 7/08 | (2006.01) | |
| C07K 14/47 | (2006.01) | |

(52) U.S. Cl.
CPC .............. *A61K 38/02* (2013.01); *A61P 35/04* (2018.01); *C07K 7/08* (2013.01); *C07K 14/4702* (2013.01)

(58) Field of Classification Search
None
See application file for complete search history.

(56) References Cited

U.S. PATENT DOCUMENTS

2007/0083334 A1* 4/2007 Mintz ..................... G06F 19/24
702/19

FOREIGN PATENT DOCUMENTS

| CN | 104762301 A | 7/2015 |
| KR | 10-2011-0052184 | 5/2011 |
| KR | 10-2016-0047735 | 5/2016 |

OTHER PUBLICATIONS

Epping et al., "TSPYL5 suppresses p53 levels and function by physical interaction with USP7," *Nature Cell Biology*, vol. 13, No. 1, pp. 102-108, 2011 (including Supplementary Information).
NCBI, GenBank Accession No. EAW91759.1, Mar. 23, 2015, 2 pages.

\* cited by examiner

Primary Examiner — Jeanette M Lieb
(74) Attorney, Agent, or Firm — Klarquist Sparkman, LLP

(57) ABSTRACT

The present invention relates to a peptide suppressing the phosphorylation of threonine (T120), the 120th residue of TSPYL5 (testis-specific Y-like protein 5), which is specifically as follows. The present inventors constructed T120D, the mutant of the 120th residue threonine (T120) of TSPYL5, and T120A-TSPYL5 gene and then transfected cells with them in order to investigate the effect of phosphorylation on T120 residue. As a result, wild-type TSPYL5 and T120D moved into nucleus and stayed there. But in the case of T120A-TSPYL5, TSPYL5 did not move into nucleus and instead it was expressed only in cytoplasm. The protein could not bind to AKT, either. Instead, ubiquitination of TSPYL5 was increased but SUMOylation was inhibited. Also, the expressions of ALDH1-A1, -A3, CD44 gene and protein were reduced, and thereby the growth and metastasis of lung cancer cells were suppressed and sphere formation was reduced. Based on the observation above, the inventors constructed the peptide composed of the amino acid sequences represented by SEQ. ID. NO: 43 or NO: 44 that could inhibit phosphorylation of the 120th residue threonine of TSPYL5. The said peptide can be effectively used as a composition for the inhibition of cancer cell growth, metastasis, and cancer stem cell growth.

8 Claims, 11 Drawing Sheets
Specification includes a Sequence Listing.

[Fig. 1a]
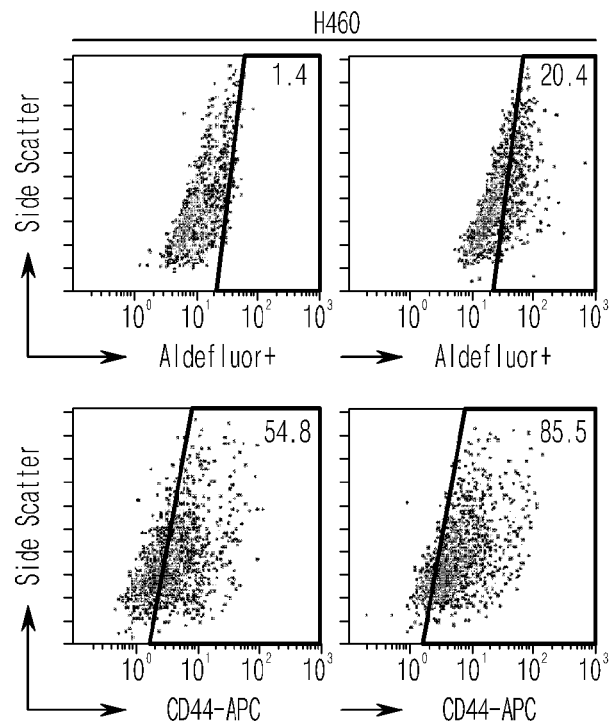
[Fig. 1b]
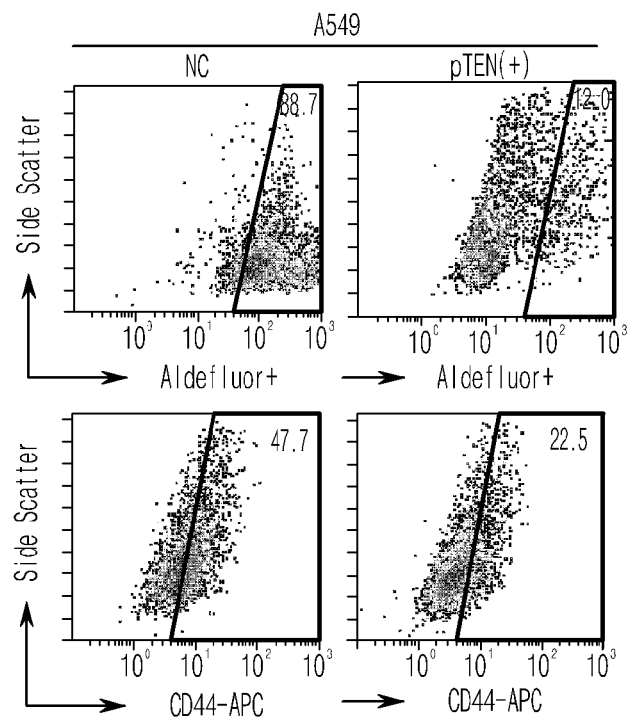

[Fig. 1c]
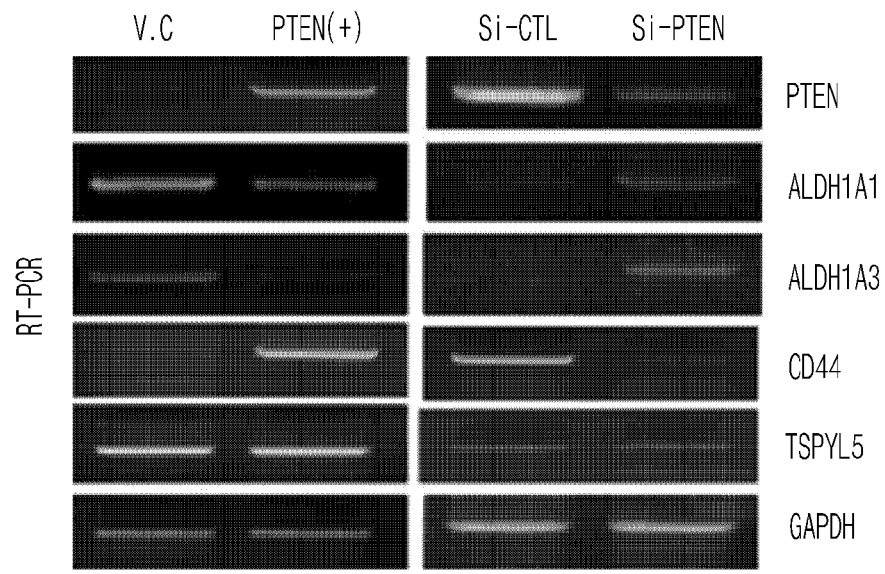
[Fig. 1d]
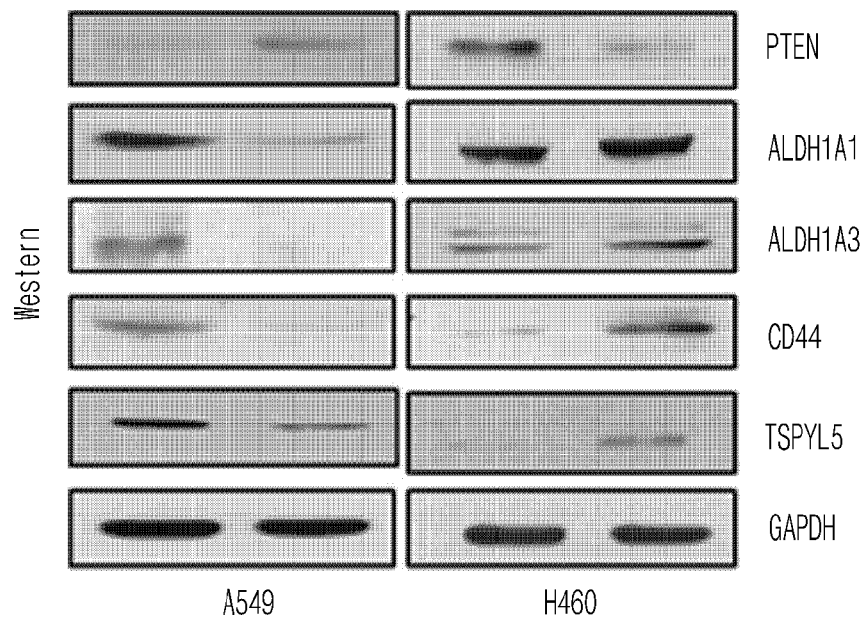

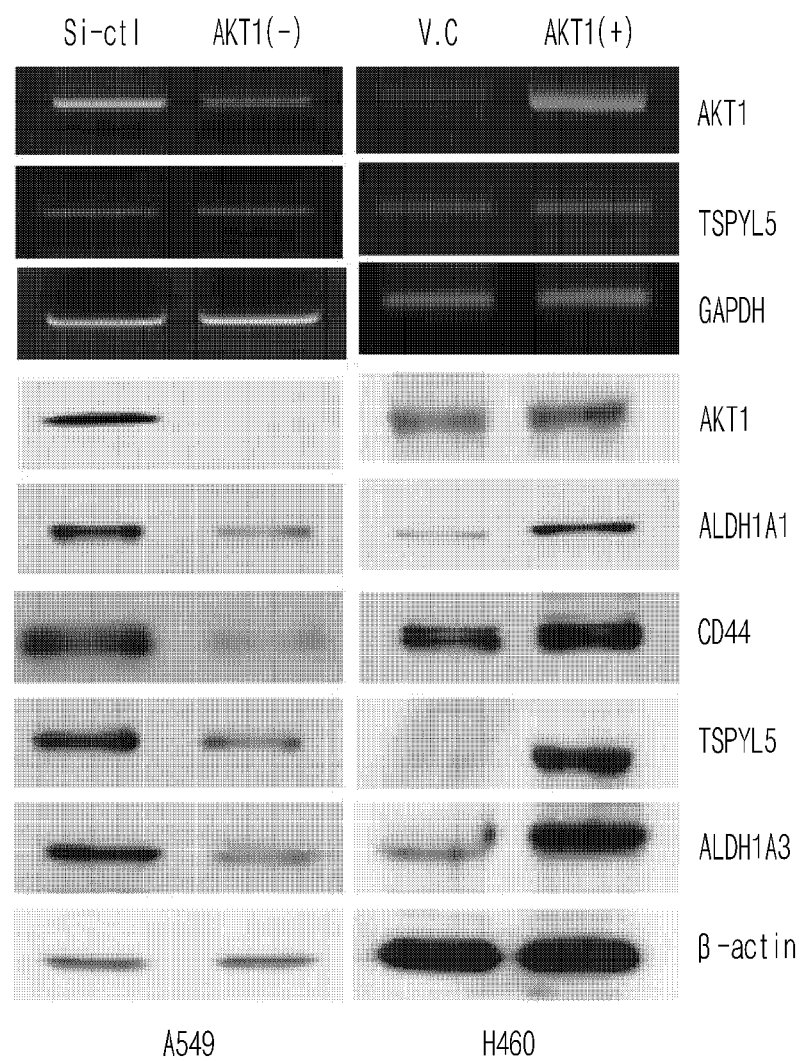
[Fig. 2a]

[Fig. 2b]
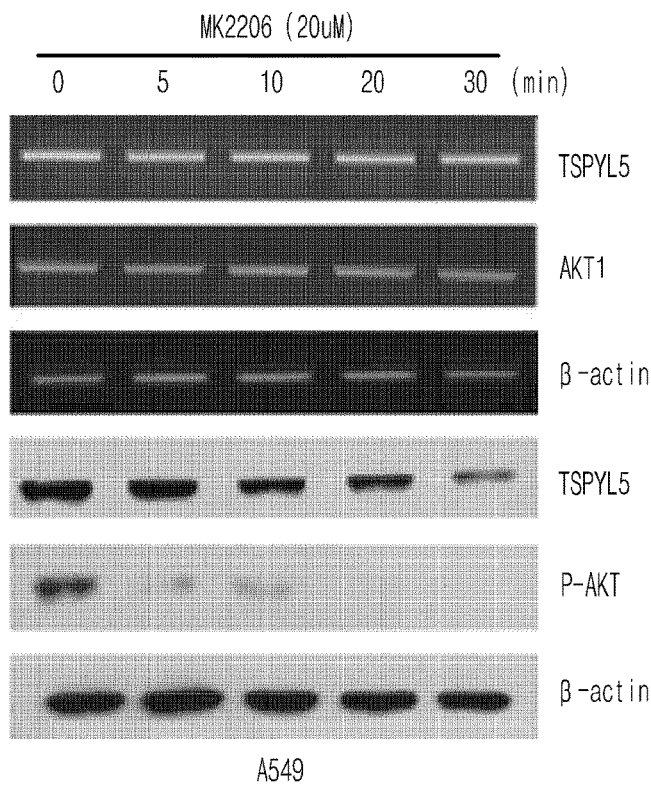
[Fig. 3a]
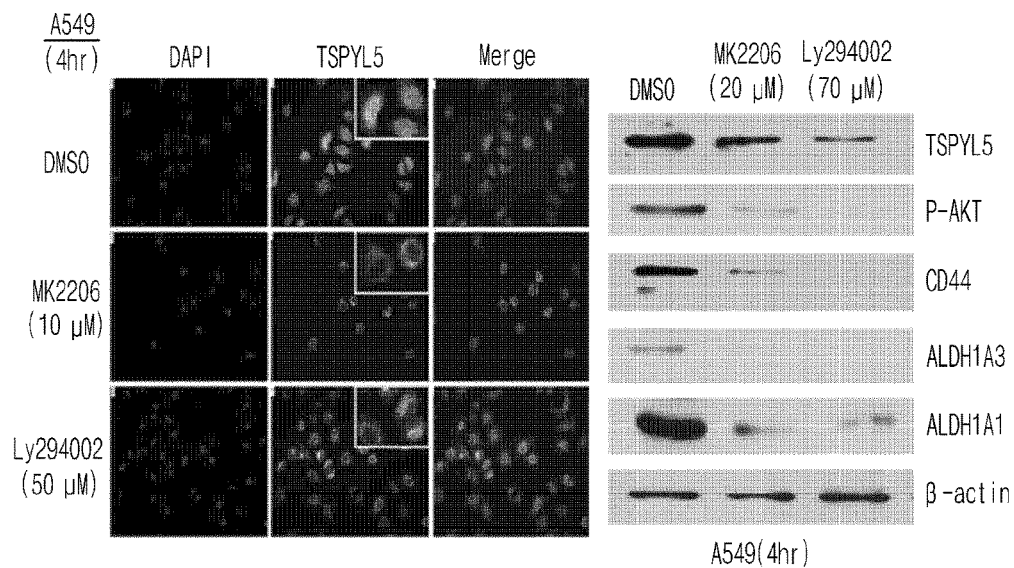

[Fig. 3b]
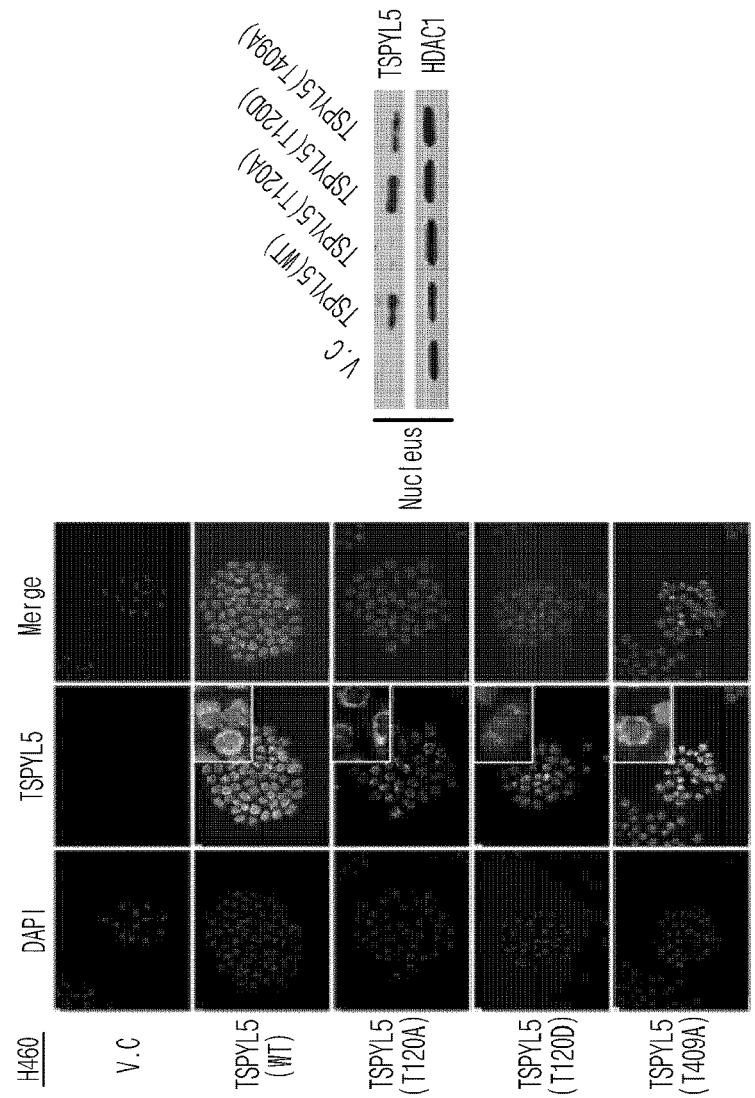
[Fig. 3c]
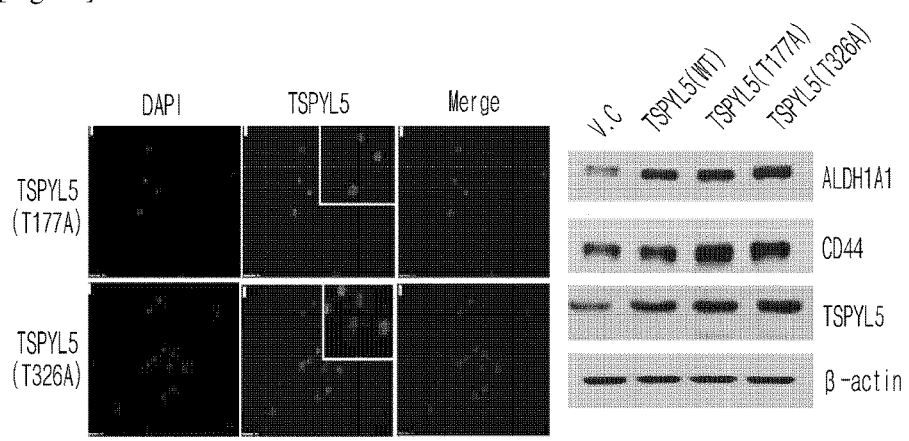

[Fig. 4]
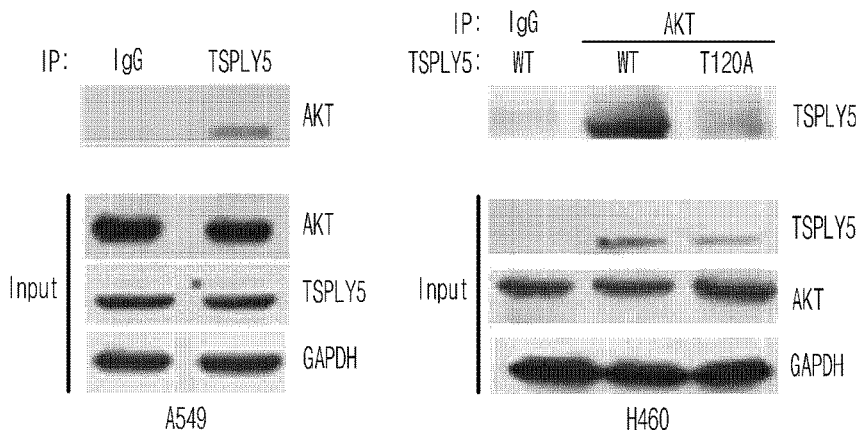
[Fig. 5]
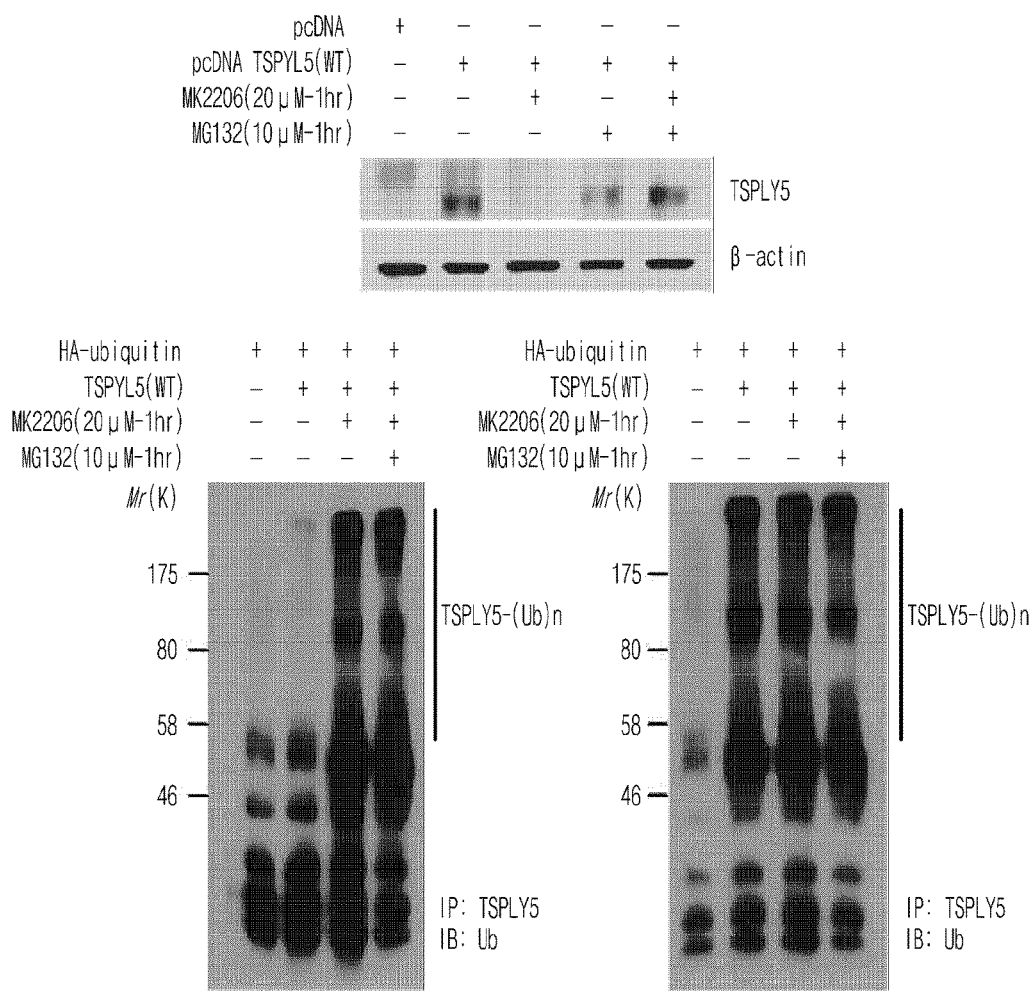

[Fig. 6a]
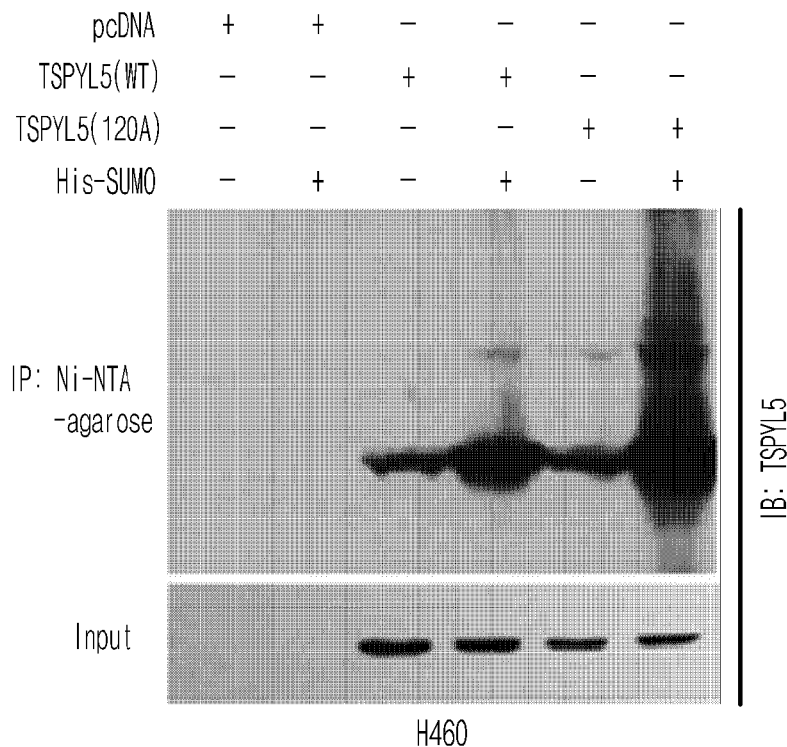
[Fig. 6b]
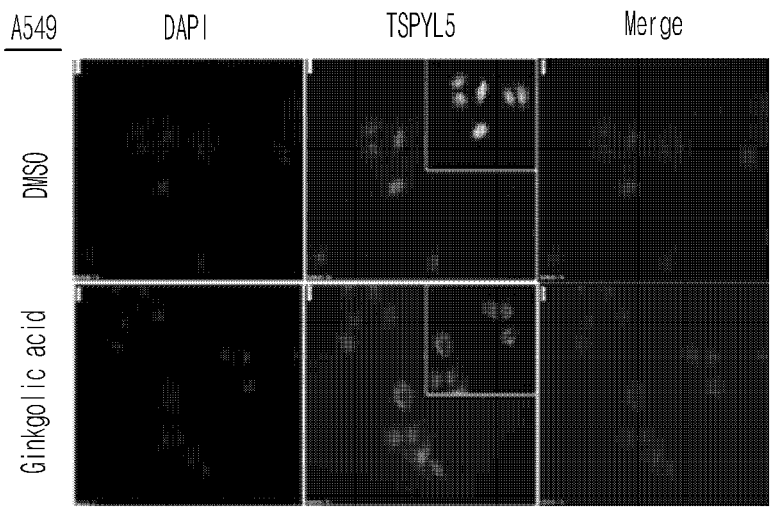

[Fig. 7a]
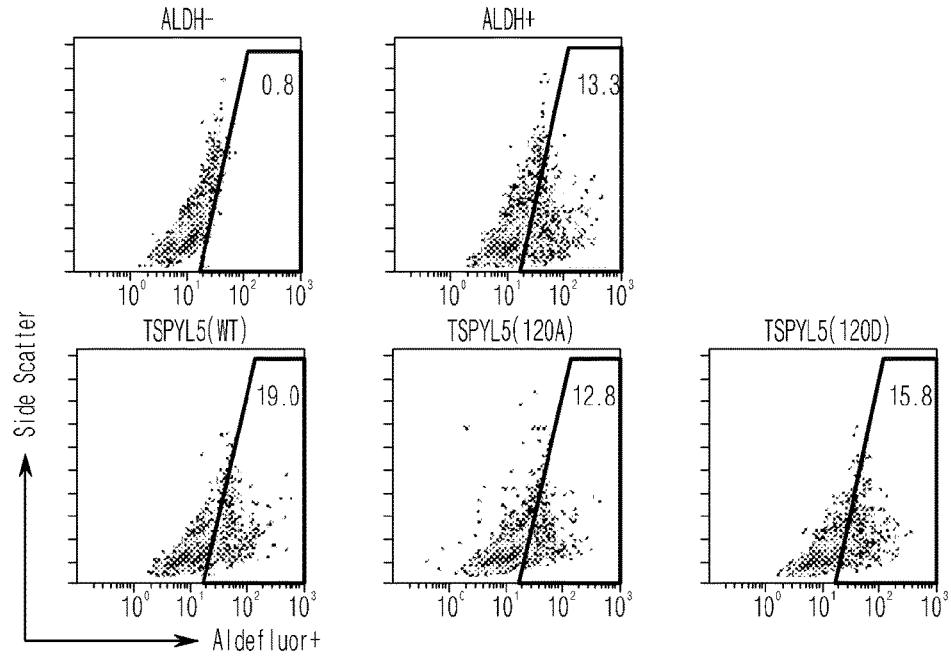
[Fig. 7b]
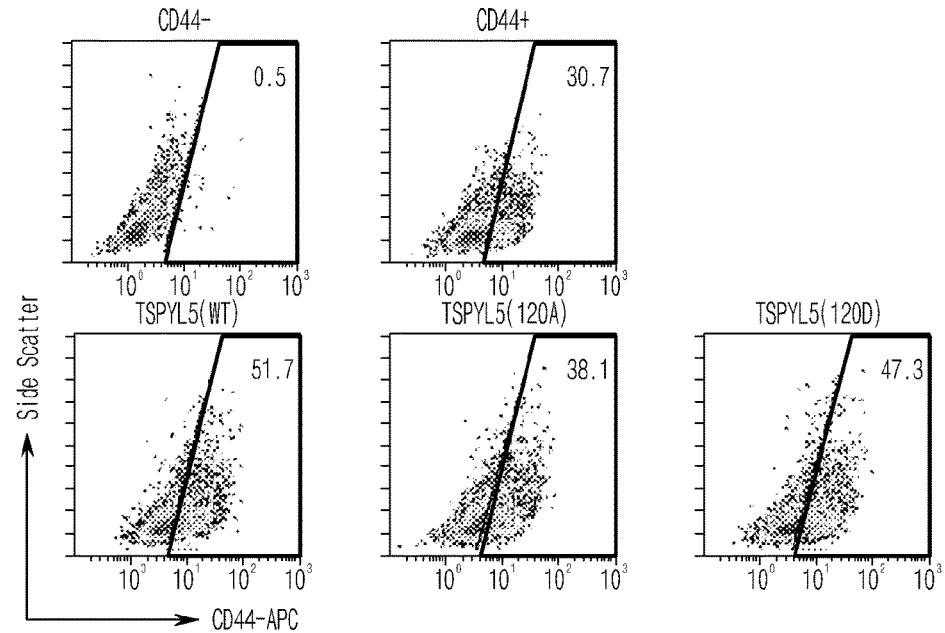

[Fig. 7c]
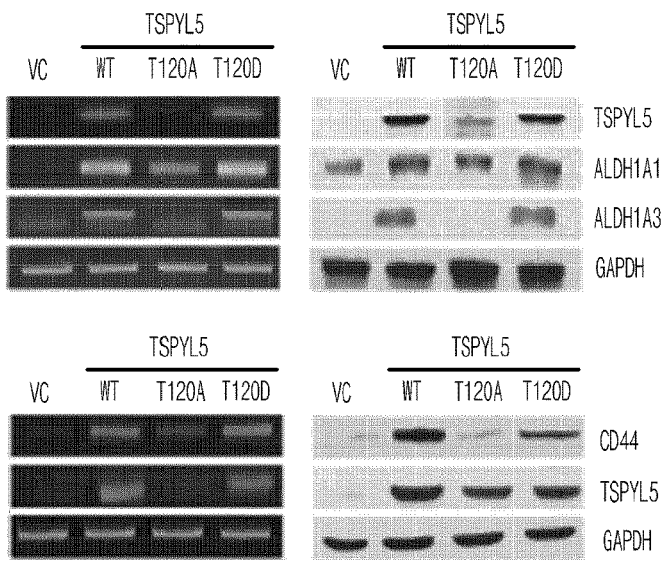
[Fig. 8a]
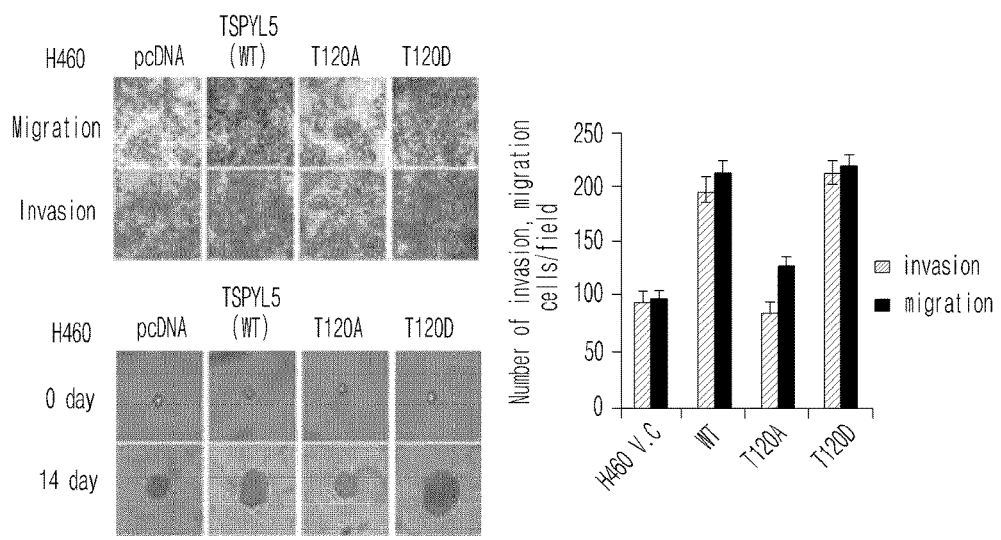
[Fig. 8b]
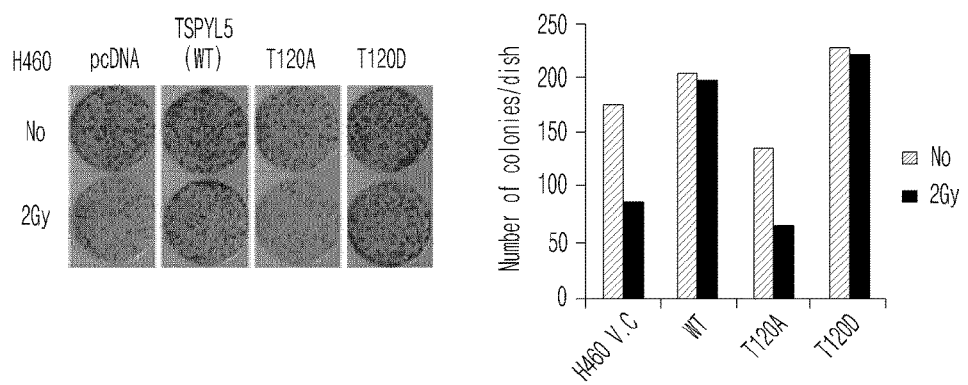

[Fig. 9]
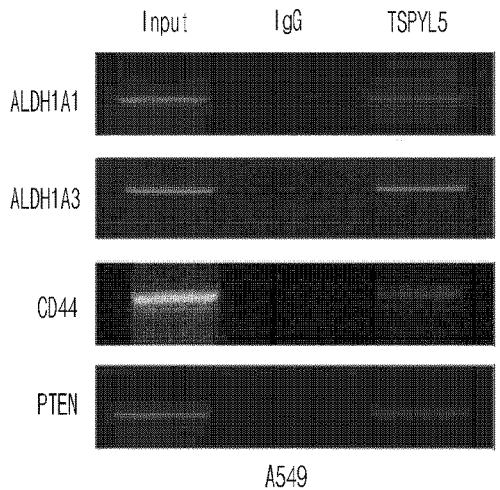
[Fig. 10]
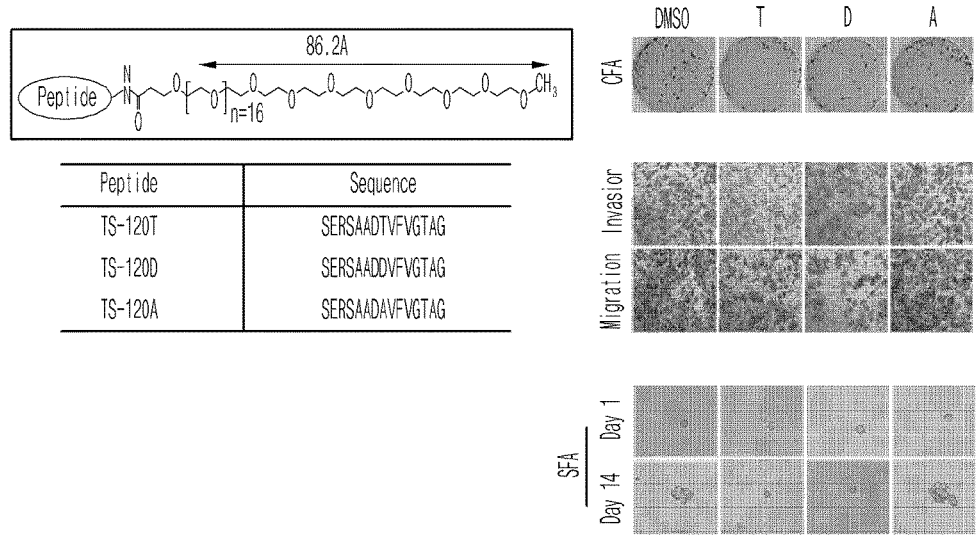
| Peptide | Sequence |
|---------|----------|
| TS-120T | SERSAADTVFVGTAG |
| TS-120D | SERSAADDVFVGTAG |
| TS-120A | SERSAADAVFVGTAG |
[Fig. 11]
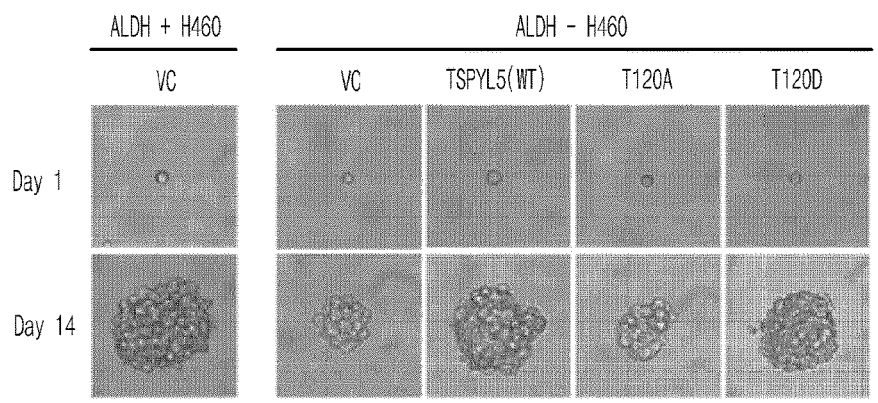

[Fig. 12]
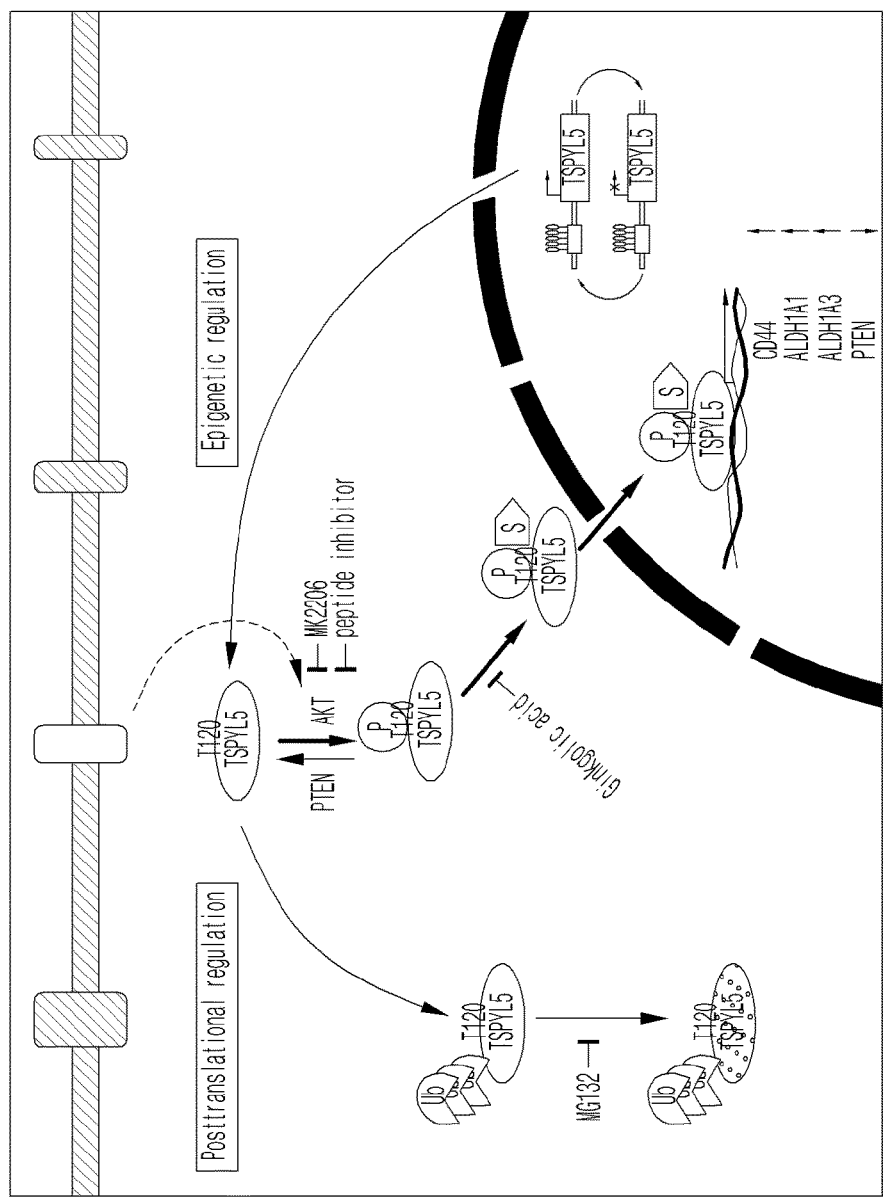

SEQUENCE LISTING

```
<160> NUMBER OF SEQ ID NOS: 45

<210> SEQ ID NO 1
<211> LENGTH: 27
<212> TYPE: DNA
<213> ORGANISM: Artificial Sequence
<220> FEATURE:
<223> OTHER INFORMATION: TSPYL5_primer F

<400> SEQUENCE: 1
cttaagctta tgagcggccg aagtcgg                                        27

<210> SEQ ID NO 2
<211> LENGTH: 28
<212> TYPE: DNA
<213> ORGANISM: Artificial Sequence
<220> FEATURE:
<223> OTHER INFORMATION: TSPYL5_primer R

<400> SEQUENCE: 2
tggaattcgt gttggattgg ctcacccc                                       28

<210> SEQ ID NO 3
<211> LENGTH: 29
<212> TYPE: DNA
<213> ORGANISM: Artificial Sequence
<220> FEATURE:
<223> OTHER INFORMATION: PTEN_primer R

<400> SEQUENCE: 3
atataagctt atgacagcca tcatcaaag                                      29

<210> SEQ ID NO 4
<211> LENGTH: 33
<212> TYPE: DNA
<213> ORGANISM: Artificial Sequence
<220> FEATURE:
<223> OTHER INFORMATION: PTEN_primer R

<400> SEQUENCE: 4
atatgaattc tcagactttg taatttgtgt atg                                 33

<210> SEQ ID NO 5
<211> LENGTH: 19
<212> TYPE: DNA
<213> ORGANISM: Artificial Sequence
<220> FEATURE:
<223> OTHER INFORMATION: AKT1_primer F

<400> SEQUENCE: 5
atgagcgacg tggctattg                                                 19

<210> SEQ ID NO 6
<211> LENGTH: 20
<212> TYPE: DNA
```

```
<213> ORGANISM: Artificial Sequence
<220> FEATURE:
<223> OTHER INFORMATION: AKT1_primer R

<400> SEQUENCE: 6
tcaggccgtg ccgctggccg                                                    20

<210> SEQ ID NO 7
<211> LENGTH: 38
<212> TYPE: DNA
<213> ORGANISM: Artificial Sequence
<220> FEATURE:
<223> OTHER INFORMATION: T120A_primer F

<400> SEQUENCE: 7
gagcgcctgg ccgcagacgc tgtcttcgtg ggaacagc                                38

<210> SEQ ID NO 8
<211> LENGTH: 38
<212> TYPE: DNA
<213> ORGANISM: Artificial Sequence
<220> FEATURE:
<223> OTHER INFORMATION: T120A_primer R

<400> SEQUENCE: 8
gctgttccca cgaagacagc gtctgcggcc aggcgctc                                38

<210> SEQ ID NO 9
<211> LENGTH: 38
<212> TYPE: DNA
<213> ORGANISM: Artificial Sequence
<220> FEATURE:
<223> OTHER INFORMATION: T120D_primer F

<400> SEQUENCE: 9
gagcgcctgg ccgcagacca tgtcttcgtg ggaacagc                                38

<210> SEQ ID NO 10
<211> LENGTH: 38
<212> TYPE: DNA
<213> ORGANISM: Artificial Sequence
<220> FEATURE:
<223> OTHER INFORMATION: T120D_primer R

<400> SEQUENCE: 10
gctgttccca cgaagacatc gtctgcggcc aggcgctc                                38

<210> SEQ ID NO 11
<211> LENGTH: 33
<212> TYPE: DNA
<213> ORGANISM: Artificial Sequence
<220> FEATURE:
<223> OTHER INFORMATION: T177A_primer F

<400> SEQUENCE: 11
ggcggcaggg gagaatgcct cggtgtcagc tgg                                     33

<210> SEQ ID NO 12
<211> LENGTH: 33
<212> TYPE: DNA
<213> ORGANISM: Artificial Sequence
<220> FEATURE:
<223> OTHER INFORMATION: T177A_primer R

<400> SEQUENCE: 12
ccagctgaca ccgaggcatt ctcccctgcc gcc                                     33
```

```
<210> SEQ ID NO 13
<211> LENGTH: 34
<212> TYPE: DNA
<213> ORGANISM: Artificial Sequence
<220> FEATURE:
<223> OTHER INFORMATION: T326A_primer F

<400> SEQUENCE: 13
ggtggtgtct cgttctgctc caatccagtg gctc                              34

<210> SEQ ID NO 14
<211> LENGTH: 34
<212> TYPE: DNA
<213> ORGANISM: Artificial Sequence
<220> FEATURE:
<223> OTHER INFORMATION: T326A_primer R

<400> SEQUENCE: 14
gagccactgg attggagcag aacgagacac cacc                              34

<210> SEQ ID NO 15
<211> LENGTH: 33
<212> TYPE: DNA
<213> ORGANISM: Artificial Sequence
<220> FEATURE:
<223> OTHER INFORMATION: T409A_primer F

<400> SEQUENCE: 15
gcagccaatg gagactgctc agcctggggt gag                               33

<210> SEQ ID NO 16
<211> LENGTH: 32
<212> TYPE: DNA
<213> ORGANISM: Artificial Sequence
<220> FEATURE:
<223> OTHER INFORMATION: T409A_primer R

<400> SEQUENCE: 16
tcaccccagg ctgagcagtc tccattggct gc                                32

<210> SEQ ID NO 17
<211> LENGTH: 25
<212> TYPE: RNA
<213> ORGANISM: Artificial Sequence
<220> FEATURE:
<223> OTHER INFORMATION: TSPYL5_primer F1

<400> SEQUENCE: 17
aaagguagaa cugcaaggga uuggg                                        25

<210> SEQ ID NO 18
<211> LENGTH: 25
<212> TYPE: RNA
<213> ORGANISM: Artificial Sequence
<220> FEATURE:
<223> OTHER INFORMATION: TSPYL5_primer R1

<400> SEQUENCE: 18
cccaaucccu ugcaguucua ccuuu                                        25

<210> SEQ ID NO 19
<211> LENGTH: 19
<212> TYPE: RNA
<213> ORGANISM: Artificial Sequence
<220> FEATURE:
```

<223> OTHER INFORMATION: PTEN_primer F1

<400> SEQUENCE: 19
gauaucaaga ggauggauu                                                    19

<210> SEQ ID NO 20
<211> LENGTH: 19
<212> TYPE: RNA
<213> ORGANISM: Artificial Sequence
<220> FEATURE:
<223> OTHER INFORMATION: PTEN_primer R1

<400> SEQUENCE: 20
aauccauccu cuugauauc                                                    19

<210> SEQ ID NO 21
<211> LENGTH: 19
<212> TYPE: RNA
<213> ORGANISM: Artificial Sequence
<220> FEATURE:
<223> OTHER INFORMATION: AKT_primer F

<400> SEQUENCE: 21
gacugacacc agguauuuu                                                    19

<210> SEQ ID NO 22
<211> LENGTH: 18
<212> TYPE: RNA
<213> ORGANISM: Artificial Sequence
<220> FEATURE:
<223> OTHER INFORMATION: AKT_primer R

<400> SEQUENCE: 22
aaauaccugg ugucaguc                                                     18

<210> SEQ ID NO 23
<211> LENGTH: 21
<212> TYPE: DNA
<213> ORGANISM: Artificial Sequence
<220> FEATURE:
<223> OTHER INFORMATION: PTEN_primer F2

<400> SEQUENCE: 23
cgaactggtg taatgatatg t                                                 21

<210> SEQ ID NO 24
<211> LENGTH: 19
<212> TYPE: DNA
<213> ORGANISM: Artificial Sequence
<220> FEATURE:
<223> OTHER INFORMATION: PTEN_primer R2

<400> SEQUENCE: 24
catgaacttg tcttcccgg                                                    19

<210> SEQ ID NO 25
<211> LENGTH: 20
<212> TYPE: DNA
<213> ORGANISM: Artificial Sequence
<220> FEATURE:
<223> OTHER INFORMATION: ALDH1A1_primer F

<400> SEQUENCE: 25
tgttagctga tgccgacttg                                                   20

```
<210> SEQ ID NO 26
<211> LENGTH: 20
<212> TYPE: DNA
<213> ORGANISM: Artificial Sequence
<220> FEATURE:
<223> OTHER INFORMATION: ALDH1A1_primer R

<400> SEQUENCE: 26
ttcttagccc gctcaacact                                              20

<210> SEQ ID NO 27
<211> LENGTH: 20
<212> TYPE: DNA
<213> ORGANISM: Artificial Sequence
<220> FEATURE:
<223> OTHER INFORMATION: ALDH1A3_primer F

<400> SEQUENCE: 27
tctcgacaaa gccctgaagt                                              20

<210> SEQ ID NO 28
<211> LENGTH: 20
<212> TYPE: DNA
<213> ORGANISM: Artificial Sequence
<220> FEATURE:
<223> OTHER INFORMATION: ALDH1A3_primer R

<400> SEQUENCE: 28
tattcggcca aagcgtattc                                              20

<210> SEQ ID NO 29
<211> LENGTH: 24
<212> TYPE: DNA
<213> ORGANISM: Artificial Sequence
<220> FEATURE:
<223> OTHER INFORMATION: CD44_primer F

<400> SEQUENCE: 29
atggacaagt tttggtggca cgca                                         24

<210> SEQ ID NO 30
<211> LENGTH: 24
<212> TYPE: DNA
<213> ORGANISM: Artificial Sequence
<220> FEATURE:
<223> OTHER INFORMATION: CD44_primer R

<400> SEQUENCE: 30
tcaccccaat cttcatgtcc acat                                         24

<210> SEQ ID NO 31
<211> LENGTH: 20
<212> TYPE: DNA
<213> ORGANISM: Artificial Sequence
<220> FEATURE:
<223> OTHER INFORMATION: TSPYL5_primer F2

<400> SEQUENCE: 31
ttcggctctc caggaagttt                                              20

<210> SEQ ID NO 32
<211> LENGTH: 20
<212> TYPE: DNA
<213> ORGANISM: Artificial Sequence
<220> FEATURE:
<223> OTHER INFORMATION: TSPYL5_primer R2
```

```
<400> SEQUENCE: 32
ggggatggtt ctgaaatgct                                              20

<210> SEQ ID NO 33
<211> LENGTH: 20
<212> TYPE: DNA
<213> ORGANISM: Artificial Sequence
<220> FEATURE:
<223> OTHER INFORMATION: GAPDH_primer F

<400> SEQUENCE: 33
aagggtcatc atctctgccc                                              20

<210> SEQ ID NO 34
<211> LENGTH: 20
<212> TYPE: DNA
<213> ORGANISM: Artificial Sequence
<220> FEATURE:
<223> OTHER INFORMATION: GAPDH_primer R

<400> SEQUENCE: 34
aggggtgcta agcagttggt                                              20

<210> SEQ ID NO 35
<211> LENGTH: 23
<212> TYPE: DNA
<213> ORGANISM: Artificial Sequence
<220> FEATURE:
<223> OTHER INFORMATION: pALDH1A1_primer F

<400> SEQUENCE: 35
atttagggct tctgagatca cag                                          23

<210> SEQ ID NO 36
<211> LENGTH: 24
<212> TYPE: DNA
<213> ORGANISM: Artificial Sequence
<220> FEATURE:
<223> OTHER INFORMATION: pALDH1A1_primer R

<400> SEQUENCE: 36
acttctcatg cttttaatg ctac                                          24

<210> SEQ ID NO 37
<211> LENGTH: 23
<212> TYPE: DNA
<213> ORGANISM: Artificial Sequence
<220> FEATURE:
<223> OTHER INFORMATION: pALDH1A3_primer F

<400> SEQUENCE: 37
gcctcagctg tgcactccag gcc                                          23

<210> SEQ ID NO 38
<211> LENGTH: 24
<212> TYPE: DNA
<213> ORGANISM: Artificial Sequence
<220> FEATURE:
<223> OTHER INFORMATION: pALDH1A3_primer R

<400> SEQUENCE: 38
tggaacaaag accggaggca cgga                                         24

<210> SEQ ID NO 39
<211> LENGTH: 24
```

```
<212> TYPE: DNA
<213> ORGANISM: Artificial Sequence
<220> FEATURE:
<223> OTHER INFORMATION: pCD44_primer F

<400> SEQUENCE: 39
aatgatggat gagaagttgt atgg                                    24

<210> SEQ ID NO 40
<211> LENGTH: 24
<212> TYPE: DNA
<213> ORGANISM: Artificial Sequence
<220> FEATURE:
<223> OTHER INFORMATION: pCD44_primer R

<400> SEQUENCE: 40
gatagggctg gcatttggct cagc                                    24

<210> SEQ ID NO 41
<211> LENGTH: 24
<212> TYPE: DNA
<213> ORGANISM: Artificial Sequence
<220> FEATURE:
<223> OTHER INFORMATION: pPTEN_primer F

<400> SEQUENCE: 41
tttgggccct tgaaattcaa cggc                                    24

<210> SEQ ID NO 42
<211> LENGTH: 24
<212> TYPE: DNA
<213> ORGANISM: Artificial Sequence
<220> FEATURE:
<223> OTHER INFORMATION: pPTEN_primer R

<400> SEQUENCE: 42
gactgcattc gctctttcct tttg                                    24

<210> SEQ ID NO 43
<211> LENGTH: 15
<212> TYPE: PRT
<213> ORGANISM: Artificial Sequence
<220> FEATURE:
<223> OTHER INFORMATION: TS120T

<400> SEQUENCE: 43

Ser Glu Arg Ser Ala Ala Asp Thr Val Phe Val Gly Thr Ala Gly
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: TS120D
```

```
<400> SEQUENCE: 44

Ser Glu Arg Ser Ala Ala Asp Asp Val Phe Val Gly Thr Ala Gly
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: TS120A

<400> SEQUENCE: 45

Ser Glu Arg Ser Ala Ala Asp Ala Val Phe Val Gly Thr Ala Gly
1               5                   10                  15
```

METHOD FOR REGULATING CANCER STEM CELL GROWTH BY INHIBITING PHOSPHORYLATION OF 120TH THREONINE RESIDUE OF TSPYL5 PROTEIN, A COMPOSITION CONTAINING THE PEPTIDE SEQUENCE FUNCTIONING TO INHIBIT THE PHOSPHORYLATION AND A USE THEREOF

CROSS REFERENCE TO RELATED APPLICATIONS

This is the § 371 U.S. National Stage of International Application No. PCT/KR2017/006240, filed Jun. 15, 2017, which was published in English under PCT Article 21(2), which in turn claims the benefit of KR Patent Application No. 10-2016-0074655, filed Jun. 15, 2016, which is incorporated by reference herein in its entirety.

TECHNICAL FIELD

The present invention relates to a peptide inhibiting phosphorylation of the 120th residue threonine of TSPYL5 (testis-specific protein, Y-encoded-like 5) and a composition comprising the same for the inhibition of cancer cell growth, metastasis, or cancer stem cell growth.

BACKGROUND ART

Cancer stem cells are a self-renewal small cell group displaying pluripotent potency enabling the differentiation into various tissues and cells like general stem cells. So, with a small number of these cells, a tumor can be induced in an experimental animal model. Cancer stem cells are also highly resistant against chemotherapy and radiotherapy (B. M. Boman, M. S. Wicha, Cancer stem cells: A step toward the cure, J. Clin. Oncol. (2008) 26:2795-2799).

Cancer stem cells were first reported in acute myeloid leukemia, and later were found in general solid cancers including breast cancer, leading to the identification of solid cancer stem cells (D. Bonnet, J. E. Dick, Human acute myeloid leukemia is organized as hierarchy that originates from a primitive hematopoietic cell. Nat. Med. (1997) 3:730-737; M. Al-Hajj, M. F. Clarke, Self-renewal and tumor stem cells. Oncogene. (2003)23:7274-7284).

The cancer stem cell specific expression markers have been reported for the identification of cancer stem cells. Among them, CD133, a membrane protein, has been used as a marker to recognize and isolate cancer stem cells in brain tumor. It has been reported that a new tumor can be developed by transplanting about 100 CD133+ cells in a nude mouse (S. K. Singh, C. Hawkins, I. D. Clarke, et al, Identification of human brain tumor initiating cells. Nature (2004) 432:396-401). Another membrane protein CD44 was also proposed as a cancer stem cell marker. According to a previous report, the cells separated with CD44(+)/CD24(−)/Lineage(−) in breast cancer were grown into a xenograft tumor (M. Al-Hajj, M. S. Wicha, A. Bentino-Hernandez et al, Proc. Natl. Acad. Sci. USA (2003) 100:3983-3988). ALDH1 (aldehydrogeanse 1), the detox enzyme that can oxidize intracellular aldehyde is also a cancer cell marker (M. Magni, S. Shammah, R. Schiro. et al, Blood (1996) 87:1097-1103; N. A. Sophos, V. Vasiliou, Chem. Biol. Interact. (2003) 143-144:5-22). The activity of ALDH1 is important for isolating the population of cancer stem cells in lung cancer cell line (F. Jiang, Q. Qiu, A. Khanna et al, Mol. Cancer. Res. (2009) 7:330-338). It has been reported that the cells demonstrating high ALDH1 activity were highly self-renewal, which is the characteristics of cancer stem cells, and were actively differentiated in such cancers as breast cancer and lung cancer. The prognosis is poor in cancer patients having the tumor cells showing high ALDH1 activity (E. Charafe-Jauffret et al, Clin. Cancer. Res. (2010) 16: 45-55).

In spite of the discovery of all those cancer stem cell specific markers, the cancer stem cell specific network and mechanism have not been known yet. Thus, to prevent the recurrence and metastasis of cancer and to eliminate cancer completely, it is necessary to develop an anticancer agent that removes cancer stem cells by targeting the cancer stem cells having the characteristics of stem cells in addition to the current cancer treatment method targeting cancer cells.

TSPYL5 gene belongs to TSPYL (testis-specific protein, Y-encoded-like) family, which is highly expressed in breast cancer and is expected to play an important role in the carcinogenesis process of breast cancer (L. J. van't Veer, et al, Nature. (2002) 415:530-536). TSPYL5 is also overexpressed in lung cancer cell line, activates PTEN/AKT pathway, accelerates cell growth, and increases radiation resistance (E. J. Kim. et al., Biochem. Biophys. Res. Commun. (2010) 392(3):448-453). USP7 (deubiquitylation enzyme for p53 activation) has been reported as an interacting protein of TSPYL5. It has been found that TSPYL5 acts as an inhibitor of USP7, and thereby increases p53 degradation, which results in the poor cancer prognosis (M. T. Epping, et al., Nat. Cell Biol. (2011) 13(1):102-108). It has also been reported that TSPYL5 is associated with transcription factors of various genes including aromatase, which catalyzes the aromatization of estradiol from testosterone involved in post-menopausal breast cancer (Liu Ml, et al., Mol Endocrinol. (2013) 27(4):657-70).

Currently, the cellular physiological aspects of TSPYL5 gene and cancer stem cells have been largely identified, and a method using shRNA or siRNA to inhibit the functions of TSPYL5 protein involved in radiation resistance and cancer stem cell characteristics has been used. However, there is a still technical limit in developing an inhibitor of radiation-sensitive or radiation-resistant cancer stem cells.

Thus, the present inventors tried to establish a method to control cancer stem cells by identifying a specific amino acid residue and its variants involved in cancer stem cell characteristics and radiation resistance in TSPYL5 protein. In the course of the study, the inventors confirmed that the phosphorylation of threonine, the 120th amino acid residue of TSPYL5, was regulated by PETM/AKT and further succeeded in the construction of the mutant of the 120th residue threonine (T120) of TSPYL5, T120D- or T120A-TSPYL5. Then, cells were transfected with the constructed mutants. As a result, the present inventors confirmed that the wild-type TSPYL5 and T120D moved into nucleus and stayed there but T120A-TSPYL5 did not moved in nucleus and instead was only expressed in cytoplasm and accordingly did not bind to AKT. When the phosphorylation was not induced, ubiquitination of TSPYL5 protein was increased but SUMOylation was suppressed. Also, the expressions of the representative cancer stem cell markers ALDH1A1, ALDH1A3, and CD44 genes and proteins were reduced. In addition, the growth and metastasis of lung cancer cells were also reduced and sphere formation was suppressed. As explained hereinbefore, the inventors proved that the growth or metastasis of cancer cells or the growth of cancer stem cells could be suppressed by inhibiting the phosphorylation of threonine, the 120th residue of TSPYL5.

At last, the present inventors confirmed that the TS120T peptide represented by SEQ. ID. NO: 43 comprising the phosphorylation region 120T and its phosphorylation analogue TS120D peptide represented by SEQ. ID. NO: 44 could be effectively used as an inhibitor for the growth or metastasis of cancer cells or the growth of cancer stem cells, leading to the completion of this invention.

DISCLOSURE OF INVENTION

Technical Problem

It is an object of the present invention to provide a cancer cell control mechanism based on the control of TSPYL5 (testis-specific protein, Y-encoded-like 5) functions, and to provide a composition for inhibiting the growth or metastasis of cancer cells or cancer stem cells by suppressing phosphorylation of threonine, the 120th residue of TSPYL5 protein using the peptide or its derivatives constructed by the present inventors.

It is another object of the present invention to provide a method for treating cancer and a method for inhibiting cancer metastasis comprising the step of administering the peptide of the invention to a subject having cancer.

It is also an object of the present invention to provide a use of the peptide of the invention as a composition for preventing or treating cancer, a composition for inhibiting cancer metastasis, and a composition for inhibiting cancer stem cell growth.

Solution to Problem

To achieve the above objects, the present invention provides a peptide composed of the amino acid sequences represented by SEQ. ID. NO: 43 or SEQ. ID. NO: 44.

The present invention also provides a pharmaceutical composition for preventing or treating cancer comprising the peptide above as an active ingredient.

The present invention also provides a composition for preventing or inhibiting cancer metastasis comprising the peptide above as an active ingredient.

The present invention also provides a composition for inhibiting cancer stem cell growth comprising the peptide above as an active ingredient.

The present invention also provides a method for treating cancer containing the step of administering the peptide above to a subject having cancer.

The present invention also provides a method for preventing cancer containing the step of administering the peptide above to a subject The present invention also provides a use of the peptide above as a composition for preventing or treating cancer.

The present invention also provides a method for inhibiting cancer metastasis containing the step of administering the peptide above to a subject having cancer.

The present invention also provides a use of the peptide above as a composition for inhibiting cancer metastasis.

In addition, the present invention provides a use of the peptide above as a composition for inhibiting cancer stem cell growth.

Advantageous Effects of Invention

The present invention relates to a peptide inhibiting the phosphorylation of threonine, the 120th residue of TSPYL5 (testis-specific Y-like protein 5). The said peptide was confirmed to inhibit the growth and metastasis of lung cancer cells and the sphere formation as well, so that the peptide composed of the nucleotide sequence represented by SEQ. ID. NO: 43 or NO: 44 that can inhibit the phosphorylation of threonine, the 120th residue of TSPYL5, can be effectively used as an inhibitor of cancer cell growth, metastasis, or cancer stem cell growth.

BRIEF DESCRIPTION OF DRAWINGS

The application of the preferred embodiments of the present invention is best understood with reference to the accompanying drawings, wherein:

FIG. 1a is a diagram illustrating the changes of the expression patterns of the cancer stem cell markers ALDH1 and CD44 caused by the over-expression of PTEN gene in the lung cancer cell line H460, analyzed by flow cytometry.

FIG. 1b is a diagram illustrating the changes of the expression patterns of the cancer stem cell markers ALDH1 and CD44 caused by the over-expression of PTEN gene in the lung cancer cell line A549, analyzed by flow cytometry.

FIG. 1c is a diagram illustrating the results of analysis of the expression patterns of ALDH1 isozyme A1, A3, CD44, and TSPYL5 by RT-PCR in order to confirm the relationship between TSPYL5 gene and protein expression.

FIG. 1d is a diagram illustrating the results of analysis of the expression patterns of ALDH1 isozyme A1, A3, CD44, and TSPYL5 by Western blotting in order to confirm the relationship between TSPYL5 gene and protein expression.

FIG. 2a is a diagram illustrating the changes of the expression patterns of TSPYL5, ALDH1, and CD44 genes and proteins according to the increase or decrease of AKT expression in lung cancer cell lines H460 and A549.

FIG. 2b is a diagram illustrating the changes of the expression patterns of TSPYL5 gene and protein according to the treatment of MK2206, the AKT protein activity inhibitor.

FIG. 3a is a diagram illustrating the intracellular distribution pattern and expression of TPSYL5 according to the treatment of AKT activity inhibitor (MK2206) or PI3K activity inhibitor (LY294002).

FIG. 3b is a diagram illustrating the expression sites of TSPYL5 protein in lung cancer cells over-expressing pcDNA3.1/TSPYL5 (wild-type), pcDNA3.1/TSPYL5-120A, pcDNA3.1/TSPYL5-409A, or pcDNA3.1/TSPYL5-120D, observed by fluorescence microscope, and the changes of the expression levels of TSPLY5 and HDAC1, measured by Western blotting.

FIG. 3c is a diagram illustrating the expression sites of TSPYL5 protein in lung cancer cells over-expressing pcDNA3.1/TSPYL5-326A or pcDNA3.1/TSPYL5-177A, observed by fluorescence microscope, and the changes of the expression levels of ALDH1A1, CD44, and TSPYL5, measured by Western blotting.

FIG. 4 is a diagram illustrating the interaction of TSPYL5 protein and AKT protein in lung cancer cells over-expressing pcDNA3.1/TSPYL5 (wild-type) and pcDNA3.1/TSPYL5-120A, investigated by immunoprecipitation.

FIG. 5 is a diagram illustrating the changes of ubiquitination according to the modification of threonine, the 120th residue of TSPYL5, in lung cancer cells over-expressing pcDNA3.1/TSPYL5 (wild-type) and pcDNA3.1/TSPYL5-120A.

FIG. 6a is a diagram illustrating the changes of SUMOylation according to the modification of threonine, the 120th residue of TSPYL5, in lung cancer cells over-expressing pcDNA3.1/TSPYL5 (wild-type) and pcDNA3.1/TSPYL5-120A.

FIG. 6b is a diagram illustrating the inhibition of TSPYL5 expression in the nucleus according to the treatment of a SUMOylation inhibitor (ginkgolic acid) in the lung cancer cell line A549.

FIG. 7a is a diagram illustrating the changes of the expression patterns of the cancer stem cell markers, ALDH1 isozymes according to the modification of threonine, the 120th residue of TSPYL5, in the cells over-expressing pcDNA3.1/TSPYL5 (wild-type), pcDNA3.1/TSPYL5-120A, or pcDNA3.1/TSPYL5-12D, investigated by immunoprecipitation.

FIG. 7b is a diagram illustrating the changes of the expression patterns of the cancer stem cell markers, CD44 according to the modification of threonine, the 120th residue of TSPYL5, in the cells over-expressing pcDNA3.1/TSPYL5 (wild-type), pcDNA3.1/TSPYL5-120A, or pcDNA3.1/TSPYL5-12D, investigated by immunoprecipitation.

FIG. 7c is a diagram illustrating the changes of the expression patterns of the cancer stem cell markers, ALDH1 isozymes and CD44 according to the modification of threonine, the 120th residue of TSPYL5, in the cells over-expressing pcDNA3.1/TSPYL5 (wild-type), pcDNA3.1/TSPYL5-120A, or pcDNA3.1/TSPYL5-12D, investigated by RT-PCR and Western blotting.

FIG. 8a is a diagram illustrating the cancer cell proliferation, metastatic ability and sphere formation according to the modification of threonine, the 120th residue of TSPYL5, in the cells over-expressing pcDNA3.1/TSPYL5 (wild-type), pcDNA3.1/TSPYL5-120A, or pcDNA3.1/TSPYL5-12D.

FIG. 8b is a diagram illustrating the cancer cell proliferation and radiation resistance according to the modification of threonine, the 120th residue of TSPYL5, in the cells over-expressing pcDNA3.1/TSPYL5 (wild-type), pcDNA3.1/TSPYL5-120A, or pcDNA3.1/TSPYL5-12D.

FIG. 9 is a diagram illustrating the function of TSPYL5 as a transcriptional activator, investigated by by chromatin precipitation.

FIG. 10 is a diagram illustrating the CFA (colony-forming ability), invasion/migration, and sphere formation ability (SFA) according to the treatment of TS120T, TS120A, and TS120D.

FIG. 11 is a diagram illustrating the sphere formation in ALDH negative cells separated from H460 (ALDH-H460) according to the over-expression of pcDNA3.1/TSPYL5 (wild-type), pcDNA3.1/TSPYL5-120D, or pcDNA3.1/TSPYL5-120A.

FIG. 12 is a diagram illustrating the increase mechanism of cancer stem cell formation by the phosphorylation of threonine, the 120th residue of TSPYL5.

The Sequence Listing is submitted as an ASCII text file in the form of the file named Sequence_Listing.txt, which was created on May 4, 2018, and is 9.02 KB, which is incorporated by reference herein.

BEST MODE FOR CARRYING OUT THE INVENTION

Hereinafter, the present invention is described in detail.

The amino acid sequences used in this invention are described as follows according to the IUPAC-IUB nomenclature.

Threonine: T,
Aspartic acid: D,
Alanine: A.

The present invention provides a peptide composed of the amino acid sequence represented by SEQ. ID. NO: 43 or NO: 44.

The said peptide characteristically inhibits the cancer cell proliferation, metastasis, or sphere formation, suppresses the phosphorylation of the 120th amino acid of TSPYL5, accelerates the ubiquitination of TSPYL5, and inhibits the SUMOylation thereof.

In a preferred embodiment of the present invention, when the peptide composed of the amino acid sequence represented by SEQ. ID. NO: 43 or NO: 44 was treated to cancer cells, the cancer cell growth and metastasis were reduced and the sphere formation was inhibited (see FIG. 10).

Therefore, the peptide of the invention can be effectively used as an inhibitor of cancer cell growth, metastasis, or cancer stem cell growth.

The peptide of the present invention can be synthesized by a method well known to those in the art, for example, can be synthesized by using an automatic peptide synthesizer, or can be produced by genetic engineering techniques. Particularly, a fusion gene encoding a fusion protein comprising a fusion partner and the peptide of the present invention is produced through gene manipulation. Then, a host microorganism is transfected with the fusion protein, wherein the fusion gene is expressed as a fusion protein. The peptide of the invention was cut out and separated from the fusion protein by using a protease or a necessary compound, resulting in the preparation of the target peptide. To do so, a DNA sequence encoding the amino acid residue that can be cut by such proteases as Factor Xa and enterokinase or such compounds as CNB4 and hydroxylamine can be inserted in between the fusion partner and the peptide gene of the invention.

The present invention also provides a pharmaceutical composition for preventing or treating cancer comprising the peptide composed of the amino acid sequence represented by SEQ. ID. NO: 43 or NO: 44 as an active ingredient.

The present invention also provides a composition for preventing or inhibiting cancer metastasis comprising the peptide composed of the amino acid sequence represented by SEQ. ID. NO: 43 or NO: 44 as an active ingredient.

In a preferred embodiment of the present invention, when the peptide of the invention was treated to cancer cells, the cancer cell growth and metastasis were reduced and the sphere formation was inhibited. Therefore, the composition comprising the peptide of the invention as an active ingredient can be effectively used for the prevention or treatment of cancer, or the prevention or inhibition of cancer metastasis.

The present invention also provides a composition for inhibiting cancer stem cell growth comprising the peptide composed of the amino acid sequence represented by SEQ. ID. NO: 43 or NO: 44 as an active ingredient.

The cancer stem cell above is selected by one of those cancer stem cell markers selected from the group consisting of CD133 (prominin-1; AC133), CD44 (hyaluronate receptor; Pglycoprotein 1), and ALDH1 (aldehyde dehydrogenase 1).

The pharmaceutical composition of the present invention can contain the peptide of the invention alone or in combination with one or more pharmaceutically acceptable carriers, excipients or diluents.

The said pharmaceutically acceptable carrier can include, for example, a carrier for oral administration or a carrier for parenteral administration. The carrier for oral administration can include lactose, starch, cellulose derivatives, magnesium stearate, stearic acid, etc.

In addition, the pharmaceutical composition of the present invention can contain various drug delivery materials used for oral administration. The carrier for parenteral administration can contain water, suitable oil, saline, aqueous glucose and glycol, and can further contain a stabilizer and a preservative. The suitable stabilizer includes an antioxidant such as sodium hydrogen sulfite, sodium sulfite or ascorbic acid. The suitable preservative includes benzalkonium chloride, methyl- or propyl-paraben and chlorobutanol. The pharmaceutical composition of the present invention can additionally contain a lubricant, a wetting agent, a sweetener, a flavoring agent, an emulsifying agent, and a suspending agent in addition to the above components. As other pharmaceutically acceptable carriers, it is possible to refer to what is described in the following document (Remington's Pharmaceutical Sciences, 19th ed., Mack Publishing Company, Easton, Pa., 1995).

The composition of the present invention can be administered to mammals including humans by any method. For example, the composition can be administered orally or parenterally. Parenteral administration indicates any route of administration that does not involve the digestive tract, including injection. Parenteral administration includes intravenous, intramuscular, intra-arterial, intramedullary, intradermal, intracardiac, transdermal, subcutaneous, intraperitoneal, intranasal, enteral, topical, sublingual or intrarectal administration, but not always limited thereto. Topical administration includes all routes of administration through the skin including creams, ointments, gels, and transdermal patches, but not always limited thereto.

The pharmaceutical composition of the present invention can be formulated into oral or parenteral administration preparations according to the administration route as described above.

The preparations for oral administration are exemplified by powders, granules, tablets, pills, sugar-coated tablets, capsules, liquids, gels, syrups, slurries, and suspensions, which can be formulated by the methods known to those in the art. For example, the preparations for oral administration can be obtained by combining the active ingredient with a solid excipient, then pulverizing thereof, adding suitable additives, and then processing the mixture into granules, tablets, or sugar-coated tablets. The suitable excipient is exemplified by sugars including lactose, dextrose, sucrose, sorbitol, mannitol, xylitol, erythritol and maltitol; starches including corn starch, wheat starch, rice starch and potato starch; cellulose derivatives including cellulose, methyl cellulose, sodium carboxymethyl cellulose and hydroxypropylmethyl cellulose; and fillers including gelatin and polyvinylpyrrolidone. In addition, crosslinked polyvinylpyrrolidone, agar, alginic acid or sodium alginate can be added as a disintegrant. Further, the pharmaceutical composition of the present invention can additionally include an anti-coagulant, a lubricant, a wetting agent, a flavoring agent, an emulsifying agent, and an antiseptic agent, etc.

The preparations for parenteral administration are exemplified by injections, creams, lotions, external ointments, oil agents, moisturizers, gels, eye drops, aerosols, and nasal inhalers, which can be formulated by the methods known to those in the art.

A preferred sterile injectable preparation can be a solution or suspension in a non-toxic parenterally acceptable solvent or a diluent. The pharmaceutically acceptable carriers or vehicles are exemplified by saline, buffered saline, isotonic saline (ex, monosodium phosphate, disodium phosphate, sodium chloride, potassium chloride, calcium chloride, magnesium chloride, or the mixtures thereof), Ringer's solution, dextrose, water, sterile water, glycerol, ethanol, and the mixtures thereof. Preferably, 1,3-butanediol and sterilized immobilized oil can be used as a solvent or a suspending medium. Fatty acid such as oleic acid can also be used in the preparation of injectable solutions.

Those formulations are described in the literature (Remington's Pharmaceutical Science, 15th Edition, 1975. Mack Publishing Company, Easton, Pa. 18042, Chapter 87: Blaug, Seymour), the formulary commonly known in all pharmaceutical chemistries.

The total effective dose of the composition of the invention can be administered to a patient in a single dose and can be administered by a fractionated treatment protocol administered over a prolonged period of time in multiple doses. The pharmaceutical composition of the present invention can vary in the amount of the active ingredient depending on the severity of disease. The effective dose of the peptide of the present invention is preferably 0.0001 μg~500 mg, and more preferably 0.01 μg~100 mg per kg of patient body weight per day. However, the effective dose of the peptide is generally determined by considering not only the administration pathway and administration times but also age, weight, health condition, gender, severity of disease, diet, and excretion. Therefore, those who have general knowledge of this field can determine the effective dose of the composition of the invention according to a specific purpose. The pharmaceutical composition of the present invention is not limited to a specific formulation, administration pathway, and administration method, as long as they do not change the effect of the invention.

The present invention also provides a method for treating cancer containing the step of administering the peptide composed of the amino acid sequence represented by SEQ. ID. NO: 43 or NO: 44 to a subject having cancer.

The present invention also provides a method for preventing cancer containing the step of administering the peptide composed of the amino acid sequence represented by SEQ. ID. NO: 43 or NO: 44 to a subject.

The present invention also provides a use of the peptide composed of the amino acid sequence represented by SEQ. ID. NO: 43 or NO: 44 as a composition for preventing or treating cancer.

The present invention also provides a method for inhibiting cancer metastasis containing the step of administering the peptide composed of the amino acid sequence represented by SEQ. ID. NO: 43 or NO: 44 to a subject having cancer.

The present invention also provides a use of the peptide composed of the amino acid sequence represented by SEQ. ID. NO: 43 or NO: 44 as a composition for inhibiting cancer metastasis.

In addition, the present invention provides a use of the peptide composed of the amino acid sequence represented by SEQ. ID. NO: 43 or NO: 44 as a composition for inhibiting cancer stem cell growth.

MODE FOR THE INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Construction of Over-Expressing Cells

<1-1> Construction of Vectors Over-Expressing TSPYL5, PTEN, and AKT1 Genes

The cells over-expressing TSPYL5, PTEN, and AKT1 genes were constructed as follows. First, the TSPYL5, PTEN, and AKT1 genes were obtained by reverse transcription from the mRNA originated from the lung cancer cell line A549 or H460.

Particularly, 1 ml of trisol was added to the lung cancer cell line A549 or H460, which was well mixed for 5 minutes. 200 μl of chloroform reagent was added thereto, which was well mixed again for 5 minutes. The mixture was centrifuged at 4° C. for 10 minutes. 200 μl of the supernatant was transferred into a new tube. 500 μl of isopropanol was added thereto, followed by reaction for 10 minutes at room temperature. Centrifugation was performed again at 4° C. to eliminate the supernatant. The precipitate was washed with DEPC solution containing 75% ethanol, followed by centrifugation again to eliminate the supernatant. The precipitate was dissolved in DEPC solution to obtain mRNA. The obtained mRNA was quantified by using cDNA kit (iNtRON Biotechnology). cDNA was synthesized from 1 μg of the quantified RNA by the reaction at 45° C. for 1 hour and at 95° C. for 5 minutes. PCR was performed with I-taq polymerase (iNtRON) and the prepared TSPYL5, PTEN, and AKT1 primers (Table 1) using the synthesized cDNA as a template. PCR was performed as follows; predenaturation at 94° C. for 5 minutes, denaturation at 94° C. for 1 minute, annealing at 56° C. for 1 minute, polymerization at 72° C. for 1 minute 30 seconds, 30 cycles from denaturation to polymerization, and final extension at 72° C. for 5 minutes.

TABLE 1

| Gene | Direction | Sequence(5'-3') | SEQ. ID. NO |
|---|---|---|---|
| TSPYL5 | Forward | CTTAAGCTTATGAGCGGCCGAAGTCGG | 1 |
|  | Reverse | TGGAATTCGTGTTGGATTGGCTCACCCC | 2 |
| PTEN | Forward | ATATAAGCTTATGACAGCCATCATCAAAG | 3 |
|  | Reverse | ATATGAATTCTCAGACTTTGTAATTTGTGTATG | 4 |
| AKT1 | Forward | ATGAGCGACGTGGCTATTG | 5 |
|  | Reverse | TCAGGCCGTGCCGCTGGCCG | 6 |

The TSPYL5, PTEN, and AKT genes obtained from PCR above and pcDNA3.1 (Invitrogen, USA) vector were digested with restriction enzyme and mixed, followed by ligation using a ligase. The prepared vector was selected by cloning, resulting in the construction of the over-expression vectors pcDNA3.1/TSPYL5, pcDNA3.1/PTEN, and pcDNA3.1/AKT1.

<1-2> Construction of Vectors Over-Expressing TSPYL5 Mutant

Gene mutation was induced in pcDNA3.1/TSPYL5 vector by using QuickChange MultiSite-Directed Mutagenesis kit (Agilent Technologies) in order to substitute the 120th residue threonine with alanine (120A) and with aspartic acid (120D) in TSPYL5. Particularly, PCR was performed with I-taq polymerase (iNtRON) and the primers listed in Table 2 using the pcDNA3.1/TSPYL5 vector as a template. PCR was performed as follows; predenaturation at 95° C. for 5 minutes, denaturation at 95° C. for 1 minute, annealing at 58° C. for 1 minute, polymerization at 72° C. for 15 minutes, 20 cycles from denaturation to polymerization, and final extension at 72° C. for 7 minutes. 30 μl of the obtained PCR product was added with 1 μl of DpnI and 3.5 μl of 10× buffer, followed by reaction at 37° C. for 1 hour. Then, the reactant was ligated to pcDNA3.1 by the same manner as described in Example <1-1>. As a result, pcDNA3.1/TSPYL5-T120A, pcDNA3.1/TSPYL5-T120D, pcDNA3.1/TSPYL5-T177A, pcDNA3.1/TSPYL5-T326A, and pcDNA3.1/TSPYL5-T409A were constructed.

TABLE 2

| TSPYL5 primer | Direction | Sequence(5'-3') | SEQ. ID. NO |
|---|---|---|---|
| T120A | Forward | gagcgcctggccgcagacgctgtcttcgtgggaacagc | 7 |
|  | Reverse | gctgttcccacgaagacagcgtctgcggccaggcgctc | 8 |
| T120D | Forward | gagcgcctggccgcagaccatgtcttcgtgggaacagc | 9 |
|  | Reverse | gctgttcccacgaagacatcgtctgcggccaggcgctc | 10 |
| T177A | Forward | ggcggcaggggagaatgcctcggtgtcagctgg | 11 |
|  | Reverse | ccagctgacaccgaggcattctccctgccgcc | 12 |
| T326A | Forward | ggtggtgtctcgttctgctccaatccagtggctc | 13 |
|  | Reverse | gagccactggattggagcagaacgagacaccacc | 14 |
| T409A | Forward | gcagccaatggagactgctcagcctggggtgag | 15 |
|  | Reverse | tcaccccaggctgagcagtctccattggctgc | 16 |

<1-3> Construction of Over-Expressing Cells $2 \times 10^5$ cell/ml of H460 cells were transfected with 4 μg of TSPYL5 and AKT over-expressing vector, and $2 \times 10^5$ cell/ml of A549 cells were transfected with 4 μg of PTEN over-expressing vector in penicillin-streptomycin solution (Hyclone) free medium by using Lipofectamine 2000. After 4~6 hour reaction, the medium was replaced with the medium supplemented with 100 units/ml of penicillin-streptomycin, followed by culture for 48 hours.

Example 2: Inhibition of the Expressions of TSPYL5, AKT, and PTEN

The following experiment using siRNA was performed to inhibit the intracellular expressions of TSPYL5, AKT, and PTEN.

Particularly, the expressions of TSPYL5 and AKT were inhibited in A549 cells, and the expression of PTEN was inhibited in H460 cells. $2 \times 10^5$ cells were transfected with 100 nM of each gene specific siRNA and Scrambled Stealth TM RNA molecule (negative control: siControl) in penicillin-streptomycin solution free medium using Lipofectamine RNAi MAX (Invitrogen) according to the manufacturer's protocol. After 4~6 hour reaction, the medium was replaced with the medium supplemented with 100 units/ml of penicillin-streptomycin, followed by culture for 72 hours.

TABLE 3

| Primer | Size | Sequence(5'-3') | SEQ. ID. NO | |
|---|---|---|---|---|
| siTSPYL5 | 25mer | AAAGGUAGAACUGCAAGGGAUUGGG | 17 | Invitrogen |
|  |  | CCCAAUCCCUUGCAGUUCUACCUUU | 18 |  |
| siPTEN | 21mer | GAUAUCAAGAGGAUGGAUU(dTdT) | 19 | Bioneer |
|  |  | AAUCCAUCCUCUUGAUAUC(dTdT) | 20 |  |
| siAKT | 21mer | GACUGACACCAGGUAUUUU(dTdT) | 21 | Bioneer |
|  |  | AAAUACCUGGUGUCAGUC(dTdT) | 22 |  |

In addition, 20 μM of MK2206 (Santa Cruze Biotechnology), the AKT (serine/threonine protein kinase) inhibitor, was treated thereto, followed by investigation of the inhibition of AKT phosphorylation and the inhibition of TSPYL5 expression.

Experimental Example 1: Regulation Effect of PTEN on TSPYL5 Expression

<1-1> Changes in the Expressions of ALDH and CD44 According to the Over-Expression or Inhibition of PTEN The expressions of the cancer stem cell markers ALDH1 and CD44 were measured by flow cytometry after ALDEFLUOR staining and CD44 antibody staining to investigate the changes of cancer stem cell characteristics according to the over-expression or inhibition of PTEN.

Particularly, A549 cells (VC), PTEN over-expressing A549 cells (PTEN(+)), H460 cells (si-CTL), and PTEN suppressed H460 cells (si-PTEN) were added with 0.5 ml of ALDEFLUOR assay buffer, resulting in 1×10⁶ cell/ml of mixture. 5 μl of the lysed cells and the activated ALDEFLUOR substrate was loaded respectively in two empty tubes. 500 μl of the mixture was loaded in the control tube. 5 μl of DEAB (diethylaminobenzaldehyde), the ALDH1 activity inhibitor, was added only to the control. Then, reaction was induced at 37° C. for 30 minutes. Centrifugation was performed to eliminate the supernatant. 500 μl of ALDEFLUOR assay buffer was added thereto and analyzed using FACScan at 4° C. (FIGS. 1a and 1b).

In order to compare the CD44 expression in A549 cells, cell surface staining was performed with anti-CD44 antibody-APC, followed by flow cytometry. 1×10⁶ cell/ml of A549 cells, 500 μl of PBS, and 10 μl of Anti-CD44 antibody-APC reagent were mixed, followed by reaction at 4 for 30 minutes. At this time, 10 μl of mouse F(ab')₂ IgG1-APC was reacted under the same conditions to be the control group for the non-specific antibody reaction. At this time, 10 μl of mouse F(ab')₂ IgG1-APC was reacted by the same conditions as the above, leading to the non-specific antibody reaction control. The regions displaying APC fluorescence over the control range were analyzed as CD44 expressing cells (FIGS. 1a and 1b).

As a result of the experiment above, it was confirmed that ALDEFLUOR staining and CD44 staining were reduced or increased by the over-expression or inhibition of PTEN, suggesting that the expressions of the cancer stem cell markers ALDH1 and CD44 were regulated by the over-expression or inhibition of PTEN (FIGS. 1a and 1b).

<1-2> Changes in the Expression of TSPYL5 According to the Over-Expression or Inhibition of PTEN The expressions of the cancer stem cell markers ALDH1 and CD44 mRNAs and proteins were measured in A549 cells (VC), A549 cells over-expressing PTEN(PTEN(+)), H460 cells (si-CTL), and PTEN-suppressed H460 cells (si-PTEN) to investigate the changes in the expressions of TSPYL5 gene and protein according to the over-expression or inhibition of PTEN.

Particularly, mRNA was extracted from the cells, to which 1 ml of trisol was added, followed by mixing for 5 minutes. 200 μl of chloroform reagent was added thereto, followed by mixing for 5 minutes. The mixture was centrifuged at 4° C. for 10 minutes. 200 μl of the supernatant was transferred into a new tube. Then, 500 μl of isopropanol was added thereto, followed by reaction at room temperature for 10 minutes. The mixture was centrifuged at 4° C. to remove the supernatant. The precipitate was washed with 75% ethanol containing DEPC. Centrifugation was performed again to eliminate the supernatant. The remaining precipitate was dissolved in DEPC solution, followed by quantification. cDNA was synthesized from 1 μg of the quantified RNA by the reaction at 45° C. for 1 hour and at 95° C. for 5 minutes by using a cDNA kit (iNtRON Biotechnology). PCR was performed with I-taq polymerase (iNtRON) and the primers listed in Table 4 using the synthesized cDNA as a template. PCR was performed as follows; predenaturation at 94° C. for 5 minutes, denaturation at 94° C. for 30 seconds, annealing at 56° C. for 30 seconds, polymerization at 72° C. for 30 seconds, 30 cycles from denaturation to polymerization, and final extension at 72° C. for 10 minutes. The product was loaded on 1% agarose gel to be confirmed.

TABLE 4

| Gene | Direction | Sequence(5'-3') | SEQ. ID. NO | Tm/cycle |
|---|---|---|---|---|
| PTEN | Forward | CGAACTGGTGTAATGATATGT | 23 | 57° C./30 |
|  | Reverse | CATGAACTTGTCTTCCCGG | 24 |  |
| ALDH1A1 | Forward | TGTTAGCTGATGCCGACTTG | 25 | 58° C./30 |
|  | Reverse | TTCTTAGCCCGCTCAACACT | 26 |  |
| ALDH1A3 | Forward | TCTCGACAAAGCCCTGAAGT | 27 | 58° C./30 |
|  | Reverse | TATTCGGCCAAAGCGTATTC | 28 |  |
| CD44 | Forward | ATGGACAAGTTTTGGTGGCACGCA | 29 | 57° C./30 |
|  | Reverse | TCACCCCAATCTTCATGTCCACAT | 30 |  |
| TSPYL5 | Forward | TTCGGCTCTCCAGGAAGTTT | 31 | 57° C./30 |
|  | Reverse | GGGGATGGTTCTGAAATGCT | 32 |  |

TABLE 4 -continued

| Gene | Direction | Sequence(5'-3') | SEQ. ID. NO | Tm/cycle |
|------|-----------|-----------------|-------------|----------|
| GAPDH | Forward | AAGGGTCATCATCTCTGCCC | 33 | 56° C./25 |
|  | Reverse | AGGGGTGCTAAGCAGTTGGT | 34 |  |

Western blotting was performed as follows in order to investigate the protein expression. Lysis buffer (0.05 M Tris-Cl (pH7.4), 0.15 M NaCl, 0.25% deoxycholic acid, 1% NP-40, 1 mM EDTA, and protease inhibitor cocktail) was added to the target cells, followed by reaction at 4° C. for 30 minutes. The cell lysate was centrifuged at 4° C. to obtain the supernatant. The supernatant was quantified. 40 μg of each protein was loaded on SDS-gel, followed by electrophoresis. The proteins were transferred onto nitrocellulose membrane, followed by blocking with BSA containing buffer at room temperature for 30 minutes. Then, the membrane was reacted with the primary antibody PTEN (1:1000), TSPYL5 (Santa Cruz), ALDH1A1, ALDH1A3 (Abcam), CD44, and β-actin, or GAPDH (CST) for 4 hours. Then, the membrane was reacted with the secondary antibody (1:10000). The nitrocellulose membrane was washed 5 times with PBS, followed by sensitization on the film with the detection solution.

As a result, as shown in FIGS. 1c and 1d, when PTEN was over-expressed in the lung cancer cell line A549, the cancer stem cell markers such as ALDH1A1, ALDH1A3, and CD44 genes and proteins were significantly down-regulated. In the meantime, when the PTEN expression was suppressed in the lung cancer cell line H460, the cancer stem cell markers such as ALDH1A1, ALDH1A3, and CD44 genes and proteins were up-regulated (FIGS. 1c and 1d).

The PTEN dependent changes in the expressions of TSPYL5 gene and protein were investigated in the cells. As a result, the TSPYL5 protein expression was increased or decreased by PTEN, but the TSPYL5 gene expression was not affected by PTEN.

Therefore, it was confirmed that the regulation of PTEN expression was closely related to the expressions of the cancer stem cell markers such as ALDH1A1, ALDH1A3, and CD44, and could also affect the TSPYL5 expression at the protein level.

Experimental Example 2: Regulation of TSPYL5 Expression Through the Regulation of AKT Gene Expression or the Inhibition of AKT Phosphorylation To investigate the changes in the expressions of TSPYL5 gene and protein according to the regulation of AKT gene expression and the inhibition of AKT activity in a non-small cell lung cancer cell line, the present inventors treated 20 μM of MK2206 (Santa Cruze Biotechnology), the AKT (serine/threonine protein kinase) inhibitor, to A549 cells or inhibited AKT1 by using siRNA. Then, PCR and Western blotting were performed by the same manner as described in Experimental Example 1 to investigate the changes in the expression patterns of AKT and TSPYL5 genes and proteins. In the meantime, the vector over-expressing AKT was constructed by the same manner as described in Example <1-1>, which was used for the transfection of the lung cancer cell line H460 by the same manner as described in Example <1-3>.

The same experiment as described in Experimental Example 1 was performed with the transfected cells.

As a result, as shown in FIG. 2a, the expression of TSPYL5 gene was not changed by the expression of AKT1 gene, but the expressions of TSPLY5, ALDH1A1, ALDH1A3, and CD44 were changed by AKT (FIG. 2a).

As shown in FIG. 2b, when the AKT phosphorylation was suppressed by MK2206, the expression of TSPYL5 protein was inhibited in proportion to the suppression time of AKT phosphorylation, suggesting that the TSPYL5 expression could be regulated by AKT (FIG. 2b).

Experimental Example 3: Location of TSPYL5 Expression in Cells

<3-1> Changes in the Location of TSPYL5 Expression According to the Treatment of AKT/PI3K Inhibitor $1 \times 10^5$ A549 cells placed on the culture dish with the cover glass were treated with 10 μM of MK2206 (AKT inhibitor) and 50 μM of LY294002 (PI3K inhibitor) for 4 hours. The cells were fixed in 4% paraformaldehyde solution for 20 minutes. Then, the cover glass was washed with PBS three times and then treated with 0.5% TritonX-100 solution for 5 minutes. The cover glass was washed again with PBS three times. The cells were treated with 1% BSA for 2 hours, followed by reaction with the primary antibody TSPYL5 (Santa Cruz) diluted in PBS buffer at the ratio of 1:100 for 2 hours. Then, the cells were reacted with the secondary antibody Rabbit (Cell Signaling Technology) diluted at the ratio of 1:1000 for 1 hour. The cells were washed with PBS three times, and then the nucleus was stained with DAPI solution for 5 minutes. The location and the amount of TSPYL5 expression were investigated under fluorescent microscope.

As a result, as shown in FIG. 3a, TSPYL5 protein was expressed in the nucleus and cytoplasm of A549 cells. However, when the cells were treated with AKT or PI3K inhibitor, TSPYL was not expressed in the nucleus. Western blotting was also performed by the same manner as described in Experimental Example <1-1>. As a result, when AKT or PI3K inhibitor was treated to the cells, the expressions of TSPYL5, phosphorylated AKT, CD44, ALDH1A3, and ALDH1A1 were reduced.

<3-2> Location of TSPYL5 Mutant Expression in Cells

To investigate the location of the expression of the TSPYTL5 mutant constructed in Example <1-2> in cells, $1 \times 10^5$ H460 cells were transfected with 5 μg of each pcDNA3.1/TSPYL5, pcDNA3.1/TSPYL5-120A, and pcDNA3.1/TSPYL5-120D by using Lipofectamine 2000 (Invitrogen). The expression pattern of TSPYL5 in cells was examined by the same manner as described in Experimental Example <3-1>.

As a result, as shown in FIG. 3b, it was confirmed that TSPYL5 was expressed in the nucleus and cytoplasm in the cells introduced with pcDNA3.1/TSPYL5 (wild-type) or pcDNA3.1/TSPYL5-120D (phosphorylation mimic). However, in the cells introduced with pcDNA3.1/TSPYL5-120A, the TSPYL5 expression was not observed in the nucleus. From the above results, it was confirmed that the 120th amino acid of TSPYL5 protein was phosphorylated and the phosphorylated TSPYL5 moved into the nucleus and was functioning as a transcription factor therein.

In addition, cell fractionation was performed to investigate the expression pattern of TSPYL5 in the cytoplasm and the nucleus. $1 \times 10^6$ H460 cells in a 10 cm culture plate were transfected with 5 μg of each pcDNA3.1/TSPYL5 (wild-type), pcDNA3.1/TSPYL5-120A, and pcDNA3.1/TSPYL5-

120D by using Lipofectamine 2000 (Invitrogen), followed by culture for 72 hours. Then, the cultured cells were collected by using trypsin-EDTA. The cells were washed with PBS twice and suspended in 5 ml of cold buffer A (10 mM HEPES (pH7.9), 1.5 mM $MgCl_2$, 10 mM KCl, 0.5 mM DTT) and then stayed in ice for 5 minutes. The cells were pulverized by Ultra Sonic (Pulse on: 2 sec, Pulse off: 8 sec, Total working time 30 sec), followed by centrifugation at 3500 rpm at 4 for 10 minutes to obtain the supernatant. The obtained supernatant was transferred in a new tube. The supernatant was added with RIPA buffer composed of 50 mM Tris-HCl (pH 7.5), 150 mM NaCl, 1% NP-40, and 0.5% deoxycholate, diluted at 10×, which was used as a cytoplasmic protein fraction. At this time, there were nuclei and by-products together in the centrifugation pellet. 3 ml of S1 buffer (0.25 M sucrose, 10 mM $MgCl_2$) was added to the pellet, and 3 ml of S3 buffer (0.88 M sucrose, 0.5 mM $MgCl_2$) was carefully added thereto, in order to separate layers. Centrifugation was performed again at 3500 rpm at 4° C. for 10 minutes to eliminate the supernatant. The remaining pellet was added with RIPA buffer, which stood in ice for 30 minutes. Centrifugation was performed at 2000 rpm at 4° C. for 30 minutes to collect the supernatant, which was transferred into a new tube. The obtained supernatant was used as a nucleus fraction. The obtained cytoplasmic fraction and the nucleus fraction were quantified, followed by Western blotting. At this time, tubulin, the protein which is present only in the cytoplasm, was used as a marker to confirm the cell fraction.

As a result, as shown in FIG. 3b, the TSPYL5-120A mutant wherein the 120th threonine residue was substituted with alanine could not move in the nucleus and stayed only in the cytoplasm. In the meantime, TSPYL5 (wild-type) and the threonine residue analogue TSPYL5-120D were expressed in the nucleus (FIG. 3b).

Other phosphorylation sites, the 326th threonine and the 409th threonine residues, were substituted with alanine, resulting in TSPYL5-326A and TSPYL5-409A mutants. Those mutants were introduced in H460 cells. As a result, as shown in FIG. 3c, they were all expressed in the nucleus (FIG. 3c). Western blotting was performed by the same manner as described in Experimental Example 1. As a result, as shown in FIG. 3c, the expression levels of CD44, TSPYL5, and ALDH1A1 were all increased (FIG. 3c).

Experimental Example 4: Binding Between TSPYL5 and AKT

To confirm the binding between TSPYL5 and AKT, the lung cancer cell line A549 or H460 was transfected with wild-type TSPYL5 or TSPYL5-120A, from which proteins were separated. TSPYL or AKT specific antibody was diluted at the ratio of 200:1, which was placed in a 4 rotator, followed by reaction for at least 12 hours. The prepared A+G agarose beads were added thereto, followed by further reaction for 5 hours. Centrifugation was performed at 2000 rpm, at 4° C., for 3 minutes. The supernatant was discarded and the remaining beads were washed with a protein extraction solution three times. The protein was heated at 95 and the protein binding was confirmed by Western blotting.

As a result, as shown in FIG. 4, the wild-type TSPYL5 protein was bound to AKT but the TSPYL5-120A mutant was not linked to AKT (FIG. 4). Therefore, it was suggested that AKT was bound to TSPYL5 to phosphorylate threonine, the 120th residue of TSPYL5.

Experimental Example 5: Ubiquitination Assay of TSPYL5

The ubiquitin proteasome mechanism is a proteolysis mechanism in eukaryotes, one of the post-translational modifications wherein the activity of a protein synthesized in cells can be regulated. Most (about 80%) of cellular proteins are degraded in proteasomes after ubiquitin labeling.

H460 cells were transfected with pcDNA3.1/TSPYL5 (wild-type) and pcDNA3.1/TSPYL5-120A constructed in Example 1. 48 hours later, 10 µM MK2206 was treated to the cells for 1 hour and then the cells were recovered. A protease inhibitor was added to a cell lysis solution (2% SDS, 150 mM NaCl, 10 mM Tris-HCl, pH 8.0), followed by mixing. 100 µl of the solution was added to the cells. The cells were lysed by using a sonicator. Centrifugation was performed at 13000 rpm. The supernatant was obtained, which was diluted in a diluting solution (0.01% SDS, 1.1% Triton X-100, 1.2 mM EDTA, 16.7 mM Tris-HCl (pH8.1), 167 mM NaCl) at ¹/₁₀, followed by reaction at 4° C. for 30 minutes. TSPYL5 or ubiquitin specific antibody was added thereto, followed by reaction for overnight to induce protein binding. Protein A/G agarose beads were added thereto, followed by reaction for 4 hours. The protein was washed with washing buffer (10 mM Tris-HCl pH 8.0, 1 M NaCl, 1 mM EDTA, 1% NP40) twice. The protein was mixed with loading buffer and heated at 95° C. Samples were loaded, followed by reaction with TSPYL5 or ubiquitin specific antibody to confirm the protein expression.

As a result, as shown in FIG. 5, when AKT inhibitor was treated, the phosphorylation of TSPYL5 was inhibited but the ubiquitination was increased. When TSPYL5-120A was over-expressed, the ubiquitination of TSPYL5-T120A protein was induced regardless of the AKT activity. When the proteosome inhibitor MG132 was treated, and accordingly when the 120th amino acid of TSPYL5 was phosphorylated, the protein degradation was suppressed and the non-phosphorylated TSPYL5-120A was decomposed by ubiquitin-proteosome mechanism (FIG. 5).

Experimental Example 6: SUMOylation Assay of TSPYL5

Ubiquitin protein is functioning to decompose a specific protein. Other proteins having similar structure to the ubiquitin protein, which are SUMO proteins, are involved in the regulation of protein functions including movement of the intracellular protein into the nucleus, changes of the binding protein, and changes of the DNA binding and transcription ability of the DNA transcription factor, etc. The present inventors performed SUMOylation assay in order to investigate the interaction between the TSPYL5 SUMOylation and the movement of TSPYL5 protein into the nucleus.

Particularly, the H460 cells transfected with pcDNA3.1/TSPYL5 (wild-type) and pcDNA3.1/TSPYL5-120A and additionally with His-tagged SUMO-expression vector were lysed in RIPA buffer. The supernatant was collected and reacted with His-tag affinity beads 4 hours. Then, the beads were was collected and treated with the sample buffer. Western blotting was performed, followed by TSPYL5 antibody reaction.

As a result, as shown in FIG. 6, in the lung cancer cell line H460 transfected with pcDNA3.1/TSPYL5 (wild-type), the SUMOylation was confirmed. However, in the cells expressing pcDNA3.1/TSPYL5-120A, the SUMOylation was not observed. To confirm the SUMOylation inhibition, the SUMO1 inhibitor ginkgolic acid (Abcam) was treated to A549 cells at the concentration of 3 uM for 2 hours. As a result, TSPYL5 protein was not expressed in the nucleus. The above results indicate that the ubiquitination and the SUMOylation of TSPYL5 were regulated by the phosphorylation of threonine, the 120th residue, and the migration of TSPYL5 into the nucleus was regulated by the SUMOylation (FIG. 6).

Experimental Example 7: Changes in the Expression Patterns of ALDH1 Isozyme and CD44 According to the Modification of Threonine, the 120th Amino Acid Residue of TSPYL5

In H460 cells, pcDNA3.1/TSPYL5 (wild-type) and pcDNA3.1/TSPYL5-120A or pcDNA3.1/TSPYL5-120D was over-expressed by the same manner as described in Experimental Example 1. Then, the expressions of the cancer stem cell markers ALDH1 and CD44 were investigated.

As a result, as shown in FIGS. 7a to 7c, in the cells wherein pcDNA3.1/TSPYL5-120A was over-expressed, the expressions of ALDH1A1, ALDH1A3, and CD44 genes and proteins were reduced. The activity of ALDH and the expression of CD44 were investigated by FACScan using ALDEFLUOR and CD44-APC. As a result, the expression amount of ALDH1 in the cells expressing TSPYL5 (wild-type) was 19%, while it was reduced to 12.8% in the cells expressing pcDNA3.1/TSPYL5-120A. The expression amount of CD44 in the cells expressing TSPYL5 (wild-type) was 51.7%, while it was reduced to 38.1% in the cells over-expressing pcDNA3.1/TSPYL5-120A (FIGS. 7a to 7c).

Therefore, it was confirmed that the expression levels of ALDH1 isozyme and CD44 genes and proteins could be increased by the phosphorylation of threonine, the 120th amino acid residue of TPSYL5.

Experimental Example 8: Cancer Cell Metastatic Ability According to the Modification of Threonine, the 120th Amino Acid Residue of TPSYL5

To investigate the cancer cell metastatic ability according to the modification of threonine, the 120th amino acid residue of TPSYL5, migration assay was performed by using transwell (Falcon, USA) having the pore size of 0.8 μm.

Particularly, $5 \times 10^4$ H460 cells and $5 \times 10^4$ H460 cells over-expressing pcDNA3.1/TSPYL5 (wild-type), pcDNA3.1/TSPYL5-120A, or pcDNA3.1/TSPYL5-120D constructed in Example 1 were mixed with 100 μl of serum free RPMI-1640, which were loaded in the transwell upper chamber. In the lower chamber, 500 μl of RPMI1640 supplemented with 7% FBS was loaded. Then, the two chambers were combined together. The cells were maintained in a 37° C., 5% $CO_2$ incubator for about 40 hours. Then, the membrane of the upper chamber was wiped with cotton swabs, followed by staining with crystal violet. The cells were observed under microscope.

For invasion assay, the transwell upper chamber was coated with 100 μl of matrigel (20 μg/well; BD Biosciences). Then, the rest of the process was the same as described in the migration assay above. The cells stained with crystal violet were eluted with 500 μl of 10% acetic acid. $OD_{600}$ was measured to calculate the relative migration/invasion value of H460 cells.

As a result, as shown in FIG. 8a, in the cells over-expressing TSPYL5 (wild-type) and pcDNA3.1/TSPYL5-120D, the cancer cell metastasis was well induced. However, in the cells over-expressing pcDNA3.1/TSPYL5-120A, the cancer cell metastasis was reduced, compared with that in the control H460 cells (FIG. 8a).

Experimental Example 9: Changes of Sphere Formation According to the Modification of Threonine, the 120th Amino Acid Residue of TPSYL5

To investigation the sphere formation in H460 cells over-expressing pcDNA3.1/TSPYL5 (wild-type), pcDNA3.1/TSPYL5-120A, or pcDNA3.1/TSPYL5-120D constructed in Example 1, $2 \times 10^4$ non-small cell lung cancer cells were suspended in DMEM (Invitrogen) supplemented with stem cell-permissive medium. 20 ng/ml of EGF, 20 ng/ml of basic fibroblast growth factor (bFGF), and B27 serum-free supplement (50×; Invitrogen) were added to DMEM-F12 (Invitrogen), which was cultured on the 60 mm plate pre-coated with 0.8% agar. The cells were cultured in a 37° C., 5% $CO_2$ incubator for 10 days. Then, the sphere formation was measured.

As a result, as shown in FIG. 8, the sphere formation was confirmed in the cells over-expressing TSPYL5 (wild-type) and pcDNA3.1/TSPYL5-120D, while the sphere formation or growth was suppressed in the cells over-expressing pcDNA3.1/TSPYL5-120A (FIG. 8a).

Experimental Example 10: Cancer Cell Proliferation and Radiation Sensitivity According to the Modification of Threonine, the 120th Amino Acid Residue of TPSYL5

$1 \times 10^3$ H460 cells either normal or over-expressing pcDNA3.1/TSPYL5, pcDNA3.1/TSPYL5-120A, or pcDNA3.1/TSPYL5-120D constructed in Example 1 were distributed on a 35 mm plate, followed by culture in a 37° C. 5% $CO_2$ incubator for 8 days. The cells were stained with 0.5% crystal violet for 10 minutes, followed by washing with PBS several times. Then, the cell proliferation was observed.

As a result, as shown in FIG. 8b, the cell proliferation was increased in H460 cells over-expressing TSPYL5 (wild-type) or pcDNA3.1/TSPYL5-120D, while the cell proliferation was suppressed in those cells over-expressing pcDNA3.1/TSPYL5-120A, compared with the control H460 cells. When the cells were irradiated (cobalt-60, 2Gy), the cells over-expressing pcDNA3.1/TSPYL5-120A demonstrated the suppressed cell proliferation, compared with the control H460 cells (FIG. 8b).

Experimental Example 11: Function of TSPYL5 as a Transcriptional Regulatory Factor Chromatin precipitation was performed to investigate the function of TSPYL5 as a transcriptional regulatory factor.

Particularly, A549 cells were cultured on a 100 mm plate. Before the collection, formaldehyde was treated thereto at the concentration of 1% by the volume of the medium. Reaction was induced in an incubator for 20 minutes and then the cells were washed with PBS containing a protease inhibitor twice. The cells were collected, and centrifuged. The collected cells were fixed and treated with SDS lysis buffer, followed by reaction in ice. The cells were disrupted with an ultrasonicator and the supernatant was obtained. A diluting solution (0.01% SDS, 1.1% Triton X-100, 1.2 mM EDTA, 16.7 mM Tris-HCl (pH8.1), 167 mM NaCl) was added to the cells above, followed by reaction for 30 minutes. The cells were reacted with TSPYL5 antibody for overnight. Protein A/G agarose beads were added thereto, followed by further reaction for 4 hours. The beads were collected by centrifugation, which were washed with a buffer several times and then reacted with elution buffer (20% SDS, 1 M NaHCO$_3$), followed by separation. The cells were treated with 5 M NaCl, followed by reaction at 65 for 4 hours. 2 μl of proteinase K (10 mg/ml), 0.5 M EDTA, and 1 M Tris-HCl (pH 6.5) were added thereto, followed by reaction at 45° C. for 1 hour. PCR was performed using the reactant as a template with the primers listed in Table 5. The PCR product was analyzed by agarose gel electrophoresis.

As a result, as shown in FIG. 9, the ALDH1A1, ALDH1A3, CD44, and PTEN genes affected by the TSPYL5 expression were confirmed as bound to TSPYL5, suggesting that the expressions of those genes were regulated by the TSPYL5 expressed in the nucleus (FIG. 9).

TABLE 5

| ChIP primer | Direction | Sequence(5'-3') | SEQ. ID. NO |
|---|---|---|---|
| pALDH1A1 | Forward | ATTTAGGGCTTCTGAGATCACAG | 35 |
|  | Reverse | ACTTCTCATGCTTTTAATGCTAC | 36 |
| pALDH1A3 | Forward | GCCTCAGCTGTGCACTCCAGGCC | 37 |
|  | Reverse | TGGAACAAAGACCGGAGGCACGGA | 38 |
| pCD44 | Forward | AATGATGGATGAGAAGTTGTATGG | 39 |
|  | Reverse | GATAGGGCTGGCATTTGGCTCAGC | 40 |
| pPTEN | Forward | TTTGGGCCCTTGAAATTCAACGGC | 41 |
|  | Reverse | GACTGCATTCGCTCTTTCCTTTTG | 42 |

Experimental Example 12: Inhibition of Cancer Cell Proliferation According to the Treatment of TPSYL5 Peptide From the above results, it was confirmed that the phosphorylation of TSPYL5 is an important factor to regulate the transcriptions of those genes that play an important role in cancer stem cell characteristics. Therefore, to inhibit the cancer stem cell proliferation, the inhibitor of the phosphorylation of threonine, the 120th residue of TSPYL5, can be efficient. So, the present inventors synthesized the peptide composed of 15 mer amino acids containing the 120th residue threonine of TSPYL5 shown in Table 6 and its derivatives, followed by investigation of the cancer cell proliferation inhibition effect thereof.

The TSPYL5 function inhibiting peptide contained 7 amino acid residues back and forth around the 120th T, and a mutant peptide in which T was substituted with D or A as the 120th threonine mutant was synthesized. Generally, since peptides do not have cell permeability, PEGylation was induced at the C-terminal of the peptide sequence, resulting in the synthesis of a TSPYL5 originated peptide having cell permeability, which was used for the efficacy test.

TABLE 6

| Peptide | Amino acid sequence | SEQ. ID. NO |
|---|---|---|
| TS120T | SERSAADTVFVGTAG | 43 |
| TS120D | SERSAADDVFVGTAG | 44 |
| TS120A | SERSSADAVFVGTAG | 45 |

Particularly, 1×10$^3$ A549 cells were distributed on a 35 mm plate, which were treated with 10 μM of each peptide. As for the control, DMSO was treated thereto, followed by culture in a 37° C. 5% CO$_2$ incubator for 8 days. The cells were stained with 0.5% crystal violet for 10 minutes. The cells were washed with PBS several times and then cell proliferation was investigated.

As a result, as shown in FIG. 10, the cell proliferation was significantly inhibited in those cells treated with TS120T and TS120D peptides, compared with the control. However, the cell proliferation in the cells treated with TS120A was not changed and was similar to that of the control (FIG. 10).

Experimental Example 13: Decrease of Cancer Cell Metastasis and Invasion According to the Treatment of TSPYL5 Peptide 5×10$^4$ A549 cells were mixed with 100 μl of serum-free RPMI-1640 and 10 μM of those peptides listed in Table 6. The mixture was loaded in the transwell upper chamber. In the lower chamber, 500 μl of RPMI1640 supplemented with 7% FBS was loaded. Then, the two chambers were combined together. The cells were cultured in a 37° C. 5% CO$_2$ incubator for 40 hours. The upper chamber membrane was wiped with cotton swabs, stained with crystal violet, and then observed under microscope.

For invasion assay, the transwell upper chamber was coated with 100 μl of matrigel (20 μg/well; BD Biosciences). Then, the rest of the process was the same as described in the migration assay above. The cells stained with crystal violet were eluted with 500 μl of 10% acetic acid. OD$_{600}$ was measured to calculate the relative migration/invasion value of A549 cells.

As a result, as shown in FIG. 10, in the cells over-expressing TSPYL5 (wild-type) and pcDNA3.1/TSPYL5-120D, the cancer cell metastasis was well induced. However, in the cells over-expressing pcDNA3.1/TSPYL5-120A, the cancer cell metastasis was reduced, compared with that in the control H460 cells (FIG. 8a).

As a result, as shown in FIG. 10, the metastasis and invasion were reduced according to the treatment of TS120T and TS120D peptides, compared with the control. However, the treatment of TS120A peptide did not make any big difference with the control (FIG. 10).

Experimental Example 14: Inhibition of Sphere Formation by TSPYL5 Peptide

To investigate the capacity of TSPYL5 peptide to inhibit the sphere formation, 2×10$^4$ A549 cells (non-small cell lung cancer cells) were suspended in DMEM (Invitrogen) containing stem cell-permissive medium. 20 ng/ml of EGF, 20 ng/ml of basic fibroblast growth factor (bFGF) and B27 serum-free supplement (Invitrogen) were mixed with DMEM-F12 (Invitrogen). The cells were distributed in the 96 well plate pre-coated with 0.8% agar (one cell/well), to which 10 μM of each peptide was treated, followed by culture. The cells were cultured in a 37° C. 5% $CO_2$ incubator for 10 days. Then, the sphere formation was observed.

As a result, as shown in FIG. 10, the sphere formation was not much changed in the cells treated with TS120A peptide, compared with the control. However, in the cells treated with TS120T and TS120D peptides, the sphere formation was suppressed, compared with the control (FIG. 10).

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A peptide composed of the amino acid sequence of SEQ ID NO: 43 or SEQ ID NO: 44.

2. The peptide according to claim 1, wherein the peptide inhibits TSPYL5 (testis-specific protein, Y-encoded like 5) expressing cancer cell proliferation, metastasis, or sphere formation.

3. The peptide according to claim 1, wherein the peptide inhibits the phosphorylation of the $120^{th}$ amino acid of TSPYL5.

4. The peptide according to claim 1, wherein the peptide accelerates ubiquitination but inhibits SUMOylation of TSPYL5.

5. A method for preventing or treating TSPYL5 expressing cancer, comprising administering to a patient in need thereof a therapeutically effective amount of the peptide of claim 1 as an active ingredient.

6. A method for preventing the reoccurrence of or inhibiting TSPYL5 expressing cancer metastasis, comprising administering to a patient in need thereof a therapeutically effective amount of the peptide of claim 1.

7. A method for inhibiting the growth of TSPYL5 expressing cancer stem cells comprising administering to a patient in need thereof a therapeutically effective amount of the peptide of claim 1.

8. The method of claim 7, wherein the TSPYL5 expressing cancer stem cell is selected by one of the cancer stem cell selection markers selected from the group consisting of CD133 (prominin-1; AC133), CD44 (hyaluronate receptor; P glycoprotein 1), and ALDH1 (Aldehyde dehydrogenase 1).

* * * * *